(12) United States Patent
Shi et al.

(10) Patent No.: US 6,391,599 B1
(45) Date of Patent: May 21, 2002

(54) SHAM-SENSITIVE TERMINAL OXIDASE GENE FROM XYLOSE-FERMENTING YEAST

(75) Inventors: Nian-Qing Shi, Forsyth, IL (US); Thomas W. Jeffries, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/556,601

(22) Filed: Apr. 21, 2000

(51) Int. Cl.⁷ .............................. C12P 7/06; C12N 9/04; C12N 1/14; C12N 15/00; C02H 21/04
(52) U.S. Cl. .................. 435/161; 435/190; 435/254.23; 435/254.1; 435/440; 536/23.2
(58) Field of Search .............................. 536/23.1, 23.2; 435/190, 161, 254.23, 254.1

(56) References Cited

U.S. PATENT DOCUMENTS 5,126,266 A   6/1992   Jeffries et al. .............. 435/255
6,071,729 A   6/2000   Jeffries et al. .............. 435/163

OTHER PUBLICATIONS

Huh et al. Molecular Cloning and Functional Expression of Alternative Oxidase from *Candida albicans*. Journal of Bacteriology. Jul. 1999: p. 4098–4102.*
Takayama et al. Antisense RNA. Crit Rev Biochem Mol Biol. 1990: p. 155–184.*
Sakajo et al. Structure and Regulatory Expression of A Single Copy Alternative Oxidase Gene form the Yeast *Pichia anomala*. Biosci. Biotechnol. Biochem., 63. 1999: 1889–1894.*
Jeppsson, H. et al., "Existence of Cyanide–Insensitive Respiration in the Yeast *Pichia stipitis* and Its Possible Influence on Product Formation during Xylose Utilization", *Applied and Environmental Microbiology*, 61:2596–2600 (1995).
Lu, P., et al., "Cloning and Disruption of the β–Isopropylmalate Dehydrogenase Gene (LEU2) of *Pichia stipitis* with URA3 and Recovery of the Double Auxotroph", *Appl. Microbiol. Biotechnol.*, 49:131–146 (1998).
Shi, N., et al., "Disruption of the Cytochrome c Gene in Xylose–utilizing Yeast *Pichia stipitis* Leads to Higher Ethanol Production", *Yeast*, 15:1021–1030 (1999).
Sreenath, H., et al., "2–Deoxyglucose as a Selective Agent for Depressed Mutants of *Pichia stipitis*", *Applied Biochemistry and Biotechnology*, 77:211–222 (1999).
Sreenath, H., et al., "Diminished Respiratory Growth and Enhanced Assimilative Sugar Uptake Result in Higher Specific Fermentation Rates by the Mutant *Pichia stipitis* FPL–061", *Applied Biochemistry and Biotechnology*, 63:109–116 (1997).
DATABASE EMBL Online, Hingxton, UK, AY004212, Aug. 8, 2000, Shi et al, "The SHAM–sensitive alternative respiration system in the xylose–metabolizing yeast, *Pichia stipitis*".
Jeppsson, H. et al., "Oxygen–dependent xylitol metabolism in *Pchia Stipitis*" *Applied Microbiology and Microtechnology*, vol. 53(1) 92–97 (1999).
Huh Won–Ki et al., "Molecular cloning and functional expression of alternative oxidase from *Candida albicans*" *J. of Bacteriology*, vol. 181(13) 4098–4102 (Jul. 1999).
Cho Jae–Yong, et al., "Transcriptional control of *ADH* genes in the xylose–fermenting yeast *Pichia stipitis*" *Applied and Environmental Microbiology*, vol. 65(6) 2363–2368 (Jun. 1999).

* cited by examiner

*Primary Examiner*—Ponnathapu Achutamurthy
*Assistant Examiner*—Yong Pak
(74) *Attorney, Agent, or Firm*—Michael Best & Friedrich LLP; Jill A. Fahrlander

(57) ABSTRACT

Disclosed is a SHAM-sensitive terminal oxidase (STO) gene from the xylose-fermenting yeast *Pichia stipitis*. Also disclosed is a mutant of *Pichia stipitis* in which the STO gene natively present in the wild-type yeast was disrupted. Mutants of *Pichia stipitis* having reduced expression of PsSTO were found to exhibit enhanced fermentation of xylose to ethanol.

23 Claims, 4 Drawing Sheets

SEQUENCE LISTING

```
<160> NUMBER OF SEQ ID NOS: 29

<210> SEQ ID NO 1
<211> LENGTH: 32
<212> TYPE: DNA
<213> ORGANISM: Pichia stipitis
<220> FEATURE:
<221> NAME/KEY: modified_base
<222> LOCATION: (3)
<223> OTHER INFORMATION: n represents inosine
<220> FEATURE:
<221> NAME/KEY: modified_base
<222> LOCATION: (24)
<223> OTHER INFORMATION: n represents inosine

<400> SEQUENCE: 1
atnttcctyg aatcyrtygc yggngtyccw gg                                   32

<210> SEQ ID NO 2
<211> LENGTH: 35
<212> TYPE: DNA
<213> ORGANISM: Pichia stipitis
<220> FEATURE:
<221> NAME/KEY: modified_base
<222> LOCATION: (15)
<223> OTHER INFORMATION: n represents inosine

<400> SEQUENCE: 2
acrgcytcyt cytcnargta dccracgaat ctgtg                                35

<210> SEQ ID NO 3
```

-continued

```
<211> LENGTH: 18
<212> TYPE: DNA
<213> ORGANISM: Pichia stipitis

<400> SEQUENCE: 3
gtaatacgac tatagggc                                                 18

<210> SEQ ID NO 4
<211> LENGTH: 19
<212> TYPE: DNA
<213> ORGANISM: Pichia stipitis

<400> SEQUENCE: 4
actatagggc acgcgtggt                                                19

<210> SEQ ID NO 5
<211> LENGTH: 29
<212> TYPE: DNA
<213> ORGANISM: Pichia stipitis

<400> SEQUENCE: 5
ccgttgcttc cttcatcaga cacttgcat                                     29

<210> SEQ ID NO 6
<211> LENGTH: 28
<212> TYPE: DNA
<213> ORGANISM: Pichia stipitis

<400> SEQUENCE: 6
ggtgtattct gcaacttgtt cttcttgt                                      28

<210> SEQ ID NO 7
<211> LENGTH: 33
<212> TYPE: DNA
<213> ORGANISM: Pichia stipitis

<400> SEQUENCE: 7
aagaatgcaa gtgtctgatg argaaggaag caa                                33

<210> SEQ ID NO 8
<211> LENGTH: 29
<212> TYPE: DNA
<213> ORGANISM: Pichia stipitis

<400> SEQUENCE: 8
gaacaagaag aacaagttgc agaatacac                                     29

<210> SEQ ID NO 9
<211> LENGTH: 28
<212> TYPE: DNA
<213> ORGANISM: Pichia stipitis

<400> SEQUENCE: 9
ggctcgtctt tacgtcttcg catctcat                                      28

<210> SEQ ID NO 10
<211> LENGTH: 28
<212> TYPE: DNA
<213> ORGANISM: Pichia stipitis

<400> SEQUENCE: 10
gcatgtgaag acttgaacgg gttgactt                                      28
```

```
<210> SEQ ID NO 11
<211> LENGTH: 28
<212> TYPE: DNA
<213> ORGANISM: Pichia stipitis

<400> SEQUENCE: 11
ccatcgatgg gagccgttgt ctgagaag                                            28

<210> SEQ ID NO 12
<211> LENGTH: 27
<212> TYPE: DNA
<213> ORGANISM: Pichia stipitis

<400> SEQUENCE: 12
ccatcgatgg aataggcctc tgcttgt                                             27

<210> SEQ ID NO 13
<211> LENGTH: 26
<212> TYPE: DNA
<213> ORGANISM: Pichia stipitis

<400> SEQUENCE: 13
atgcttctgt gcagactaca agagcc                                              26

<210> SEQ ID NO 14
<211> LENGTH: 26
<212> TYPE: DNA
<213> ORGANISM: Pichia stipitis

<400> SEQUENCE: 14
ttacaatttc aattcttcct tctccc                                              26

<210> SEQ ID NO 15
<211> LENGTH: 21
<212> TYPE: DNA
<213> ORGANISM: Pichia stipitis

<400> SEQUENCE: 15
ggcatgacta accaaagtga a                                                   21

<210> SEQ ID NO 16
<211> LENGTH: 22
<212> TYPE: DNA
<213> ORGANISM: Pichia stipitis

<400> SEQUENCE: 16
cgttcgctct tgtgagagca tt                                                  22

<210> SEQ ID NO 17
<211> LENGTH: 31
<212> TYPE: DNA
<213> ORGANISM: Pichia stipitis

<400> SEQUENCE: 17
cgggatccga gctgtctcat gtcccttaca a                                        31

<210> SEQ ID NO 18
<211> LENGTH: 32
<212> TYPE: DNA
<213> ORGANISM: Pichia stipitis

<400> SEQUENCE: 18
cgggatccac ctgggatgta cttctttggg tt                                       32
```

<210> SEQ ID NO 19
<211> LENGTH: 33
<212> TYPE: DNA
<213> ORGANISM: Pichia stipitis

<400> SEQUENCE: 19
ccgctcgagc cagcatagag tgaacgaaac cac         33

<210> SEQ ID NO 20
<211> LENGTH: 33
<212> TYPE: DNA
<213> ORGANISM: Pichia stipitis

<400> SEQUENCE: 20
ccgctcgagc agggagcttt agaccagcat ggt         33

<210> SEQ ID NO 21
<211> LENGTH: 22
<212> TYPE: DNA
<213> ORGANISM: Pichia stipitis

<400> SEQUENCE: 21
atgccagctc cattcgaaag gg                     22

<210> SEQ ID NO 22
<211> LENGTH: 22
<212> TYPE: DNA
<213> ORGANISM: Pichia stipitis

<400> SEQUENCE: 22
ttacttggtg gcggaagcca ag                     22

<210> SEQ ID NO 23
<211> LENGTH: 32
<212> TYPE: DNA
<213> ORGANISM: Pichia stipitis

<400> SEQUENCE: 23
ccgctcgagc ggatgcttct gtgcagacta ca          32

<210> SEQ ID NO 24
<211> LENGTH: 34
<212> TYPE: DNA
<213> ORGANISM: Pichia stipitis

<400> SEQUENCE: 24
ccgctcgagc ggttacaatt tcaattcttc cttc        34

<210> SEQ ID NO 25
<211> LENGTH: 2853
<212> TYPE: DNA
<213> ORGANISM: Pichia stipitis
<220> FEATURE:
<221> NAME/KEY: CDS
<222> LOCATION: (954)..(2027)

<400> SEQUENCE: 25
tgttcgtctt tacgtcttcg catctcatct tttcgtcttt aagttcctga ccctcgtact    60
ttcgtacttc gcacatttcc cctaatacga atggcgatca ttacgtaata ttctgccatc   120
ccaaattgct ctggatcgct gcgaggctga aacggaaagt catcatccgt tgatccttgt   180
gtcctttcgt tgtctacgcc caatcttttg caatcggaca ttaaccatcg aagtcatgct   240

-continued

```
atgttccatt ctgtcaatac aaatttgatt cacgaagcaa aaccggtgca cctcccgaca      300
acttccgcac agagcggaaa aacaatctgc tcaaactagc tggaacactt tcccaaacgg      360
ggtttgagaa cagaactgga aactggagtc atgattaat tacgctgtac ggccattggt       420
caaaatggca gcgagccagc gttcaactga tgtaaagagg aagaactcgg aaacggaata     480
tggcttccat gctctgaatg aaactccgga ttccctagct aatacccggc accccaccg      540 tatggctgta ccagtgactc ccgagacatc tgcttgtaga gtaagcgatt tcaccaaaaa    600
gtcgaattga aaacgaatcc aactatcagt ccatatttct ctaccggtct ttccatgaag    660
acatctgagt tactgttaca ctcgacaagc tacactctac taaatggctg ttccaaaaaa   720
gccccttcag atggaagtat ggccgcggaa tcaatggtat ataaataaat gtaaaattgc   780
gcaaagctaa tactcaaatt ataatattat aatattatat ctaagtctgc aatgttttttt  840 ctgttgctca tagactctcg taattcctat aaatataact gattccagtg caattccatc   900
tttatccctt ttctcctctt cctcatccag tctagcaatt caattaaatt aca atg       956
                                                                 Met
                                                                  1 ctt tct gtg cag act aca aga gcc gcc aag ttg caa cta ggt caa tta    1004
Leu Ser Val Gln Thr Thr Arg Ala Ala Lys Leu Gln Leu Gly Gln Leu
                5                   10                  15 cct ctg att gcc tac acc gcc aga agt gga aga ctt cac cac caa ttc    1052
Pro Leu Ile Ala Tyr Thr Ala Arg Ser Gly Arg Leu His His Gln Phe
            20                  25                  30 tac tcc acc gtt gct gaa aag aca gcc aac cct acg cca aac acc tca    1100
Tyr Ser Thr Val Ala Glu Lys Thr Ala Asn Pro Thr Pro Asn Thr Ser
        35                  40                  45 gat aaa act aat att ttt gat att aga acc aag gtg tac gat gag act    1148
Asp Lys Thr Asn Ile Phe Asp Ile Arg Thr Lys Val Tyr Asp Glu Thr
    50                  55                  60                  65 gat ata aga aaa cat gac gac aat cag ttt atc acc cat cct tta ttt    1196
Asp Ile Arg Lys His Asp Asp Asn Gln Phe Ile Thr His Pro Leu Phe
                70                  75                  80 cct cat cct acg ttt tcg cag gaa gat tgt ttg aaa gtt ggt tac gaa    1244
Pro His Pro Thr Phe Ser Gln Glu Asp Cys Leu Lys Val Gly Tyr Glu
            85                  90                  95 cat cgt cct cct cgg act ttt ggt gac aaa atg gct ttc aga ggc att    1292
His Arg Pro Pro Arg Thr Phe Gly Asp Lys Met Ala Phe Arg Gly Ile
        100                 105                 110 gaa ctt gtc aga ggt tct ttc gac ttt gtc acc ggt tac aag aag cca    1340
Glu Leu Val Arg Gly Ser Phe Asp Phe Val Thr Gly Tyr Lys Lys Pro
    115                 120                 125 aag aca cag gct gat atc gat tca ggt ttt aaa ggt acc aga tac gag    1388
Lys Thr Gln Ala Asp Ile Asp Ser Gly Phe Lys Gly Thr Arg Tyr Glu
130                 135                 140                 145 atg aca gaa ggt aaa tgg ttg acc aga tgt ata ttc tta gaa agt att    1436
Met Thr Glu Gly Lys Trp Leu Thr Arg Cys Ile Phe Leu Glu Ser Ile
                150                 155                 160 gct gga gtt cca ggt gcc gtt gct tcc ttc atc aga cac ttg cat tct    1484
Ala Gly Val Pro Gly Ala Val Ala Ser Phe Ile Arg His Leu His Ser
            165                 170                 175 tta cgt ttg ttg aag aga gac aaa gcc tgg atc gaa acc tta ctt gat    1532
Leu Arg Leu Leu Lys Arg Asp Lys Ala Trp Ile Glu Thr Leu Leu Asp
        180                 185                 190 gaa gca ttc aac gaa aga atg cat tta ctt acc ttc atc aag att ggc    1580
Glu Ala Phe Asn Glu Arg Met His Leu Leu Thr Phe Ile Lys Ile Gly
    195                 200                 205 aaa cct agt tgg ttc acc aga aca atc atc tac gtc ggc caa ggt gta   1628
```

```
Lys Pro Ser Trp Phe Thr Arg Thr Ile Ile Tyr Val Gly Gln Gly Val
210                 215                 220                 225 ttc tgc aac ttg ttc ttc ttg ttc tac ttg gcc aac cct aag tat tgt    1676
Phe Cys Asn Leu Phe Phe Leu Phe Tyr Leu Ala Asn Pro Lys Tyr Cys
                    230                 235                 240 cac agg ttt gtt ggc tac ctt gaa gaa gag gct gtt agt acc tac act    1724
His Arg Phe Val Gly Tyr Leu Glu Glu Glu Ala Val Ser Thr Tyr Thr
                245                 250                 255 cat ttc gtc cat gaa tta caa tca ggt aag ctt ccc aag ttt gag aac    1772
His Phe Val His Glu Leu Gln Ser Gly Lys Leu Pro Lys Phe Glu Asn
            260                 265                 270 atc aag att cca acc att gca tgg caa tac tgg cca gag ttg acc gag    1820
Ile Lys Ile Pro Thr Ile Ala Trp Gln Tyr Trp Pro Glu Leu Thr Glu
        275                 280                 285 aat tcg tcc atg ttg gac ttg att tta aga atc aga gcc gac gaa gcc    1868
Asn Ser Ser Met Leu Asp Leu Ile Leu Arg Ile Arg Ala Asp Glu Ala
290                 295                 300                 305 aag cac aga gaa gtc aac cac acc ttg gcc aat tta gat caa aga aag    1916
Lys His Arg Glu Val Asn His Thr Leu Ala Asn Leu Asp Gln Arg Lys
                    310                 315                 320 gac aga aat cca ttt ggg ttg gca att ccg gat ctc aag gaa ccg caa    1964
Asp Arg Asn Pro Phe Gly Leu Ala Ile Pro Asp Leu Lys Glu Pro Gln
                325                 330                 335 ccc gaa agt ggc tta aag gtt acg aaa ccc cac ggc tgg gag aag gaa    2012
Pro Glu Ser Gly Leu Lys Val Thr Lys Pro His Gly Trp Glu Lys Glu
            340                 345                 350 gaa ttg aaa ttg taa gaattgctca ggtttcccga tttctttcta catcattttt    2067
Glu Leu Lys Leu
        355 gtatcgttgt tcatagttag gttttacga agaatgaagt catgattagc acgaagttga   2127 ttgcaccgta gtagccgctg gaaacagcta cagtttaatc gagagtagct gcaagtcaga   2187 cctgtatgga atcaaaatcg gagttgcagc aatatcaaat cccgcgcaag ttgagagaca   2247 tctcttagca atatcgagac caatacgatg aagttaggaa ttggccgata agagaacgga   2307 gaaatattat acaaagcaga acctggggct ttgcaggata aagaggaaat ggaagcaagg   2367 ctacgagaaa agcacgaaga atgggggact ggaccagtag ttatttaggt gcgattaaca   2427 ttgataatat tgctacagag ccaaacgcca cgaagctttc cgcaaagtag cagtgctgtg   2487 tacgtatttt acgggttcc atacgttgca gcaacgggtt cttgatttcc gctgttacta    2547 gagcaaagat agaggatgga aaataagtca gaccacctt gtcaattgga ctaatattat    2607 atgagaagcg taagactaaa aaatgtacga gagcaaaaga aattatacca aaaattgcaa   2667 acaccatttt tttccggtag caaaacacaa acgtcggtct tctgaagtca acccgttcaa   2727 gtcttcacat gcaagggcga attccagcac actggcggcc gtactagtgg gatccgagct   2787 cggtccaact tgatgcatac ttgagtattt ataatgtcac ctaatactgg gcgtaatcat   2847 ggcata                                                               2853
```

<210> SEQ ID NO 26
<211> LENGTH: 357
<212> TYPE: PRT
<213> ORGANISM: Pichia stipitis

<400> SEQUENCE: 26

```
Met Leu Ser Val Gln Thr Thr Arg Ala Ala Lys Leu Gln Leu Gly Gln
1               5                   10                  15

Leu Pro Leu Ile Ala Tyr Thr Ala Arg Ser Gly Arg Leu His His Gln
```

```
                20                  25                  30
Phe Tyr Ser Thr Val Ala Glu Lys Thr Ala Asn Pro Thr Pro Asn Thr
            35                  40                  45
Ser Asp Lys Thr Asn Ile Phe Asp Ile Arg Thr Lys Val Tyr Asp Glu
 50                  55                  60
Thr Asp Ile Arg Lys His Asp Asn Gln Phe Ile Thr His Pro Leu
 65                  70                  75                  80
Phe Pro His Pro Thr Phe Ser Gln Glu Asp Cys Leu Lys Val Gly Tyr
                85                  90                  95
Glu His Arg Pro Pro Arg Thr Phe Gly Asp Lys Met Ala Phe Arg Gly
               100                 105                 110
Ile Glu Leu Val Arg Gly Ser Phe Asp Phe Val Thr Gly Tyr Lys Lys
               115                 120                 125
Pro Lys Thr Gln Ala Asp Ile Asp Ser Gly Phe Lys Gly Thr Arg Tyr
           130                 135                 140
Glu Met Thr Glu Gly Lys Trp Leu Thr Arg Cys Ile Phe Leu Glu Ser
145                 150                 155                 160
Ile Ala Gly Val Pro Gly Ala Val Ala Ser Phe Ile Arg His Leu His
               165                 170                 175
Ser Leu Arg Leu Leu Lys Arg Asp Lys Ala Trp Ile Glu Thr Leu Leu
           180                 185                 190
Asp Glu Ala Phe Asn Glu Arg Met His Leu Leu Thr Phe Ile Lys Ile
               195                 200                 205
Gly Lys Pro Ser Trp Phe Thr Arg Thr Ile Ile Tyr Val Gly Gln Gly
           210                 215                 220
Val Phe Cys Asn Leu Phe Phe Leu Phe Tyr Leu Ala Asn Pro Lys Tyr
225                 230                 235                 240
Cys His Arg Phe Val Gly Tyr Leu Glu Glu Ala Val Ser Thr Tyr
               245                 250                 255
Thr His Phe Val His Glu Leu Gln Ser Gly Lys Leu Pro Lys Phe Glu
           260                 265                 270
Asn Ile Lys Ile Pro Thr Ile Ala Trp Gln Tyr Trp Pro Glu Leu Thr
       275                 280                 285
Glu Asn Ser Ser Met Leu Asp Leu Ile Leu Arg Ile Arg Ala Asp Glu
       290                 295                 300
Ala Lys His Arg Glu Val Asn His Thr Leu Ala Asn Leu Asp Gln Arg
305                 310                 315                 320
Lys Asp Arg Asn Pro Phe Gly Leu Ala Ile Pro Asp Leu Lys Glu Pro
                   325                 330                 335
Gln Pro Glu Ser Gly Leu Lys Val Thr Lys Pro His Gly Trp Glu Lys
               340                 345                 350
Glu Glu Leu Lys Leu
           355

<210> SEQ ID NO 27
<211> LENGTH: 13
<212> TYPE: PRT
<213> ORGANISM: Pichia stipitis

<400> SEQUENCE: 27

Ile Phe Leu Glu Ser Ile Ala Gly Val Pro Gly Met Val
 1               5                  10

<210> SEQ ID NO 28
<211> LENGTH: 13
```

-continued

```
<212> TYPE: PRT
<213> ORGANISM: Pichia stipitis

<400> SEQUENCE: 28

Ile Phe Leu Glu Ser Val Ala Gly Val Pro Gly Met Val
 1               5                  10

<210> SEQ ID NO 29
<211> LENGTH: 12
<212> TYPE: PRT
<213> ORGANISM: Pichia stipitis

<400> SEQUENCE: 29

His Arg Phe Val Gly Tyr Leu Glu Glu Glu Ala Val
 1               5                  10
```

SHAM-SENSITIVE TERMINAL OXIDASE GENE FROM XYLOSE-FERMENTING YEAST

STATEMENT REGARDING FEDERALLY SPONSORED RESEARCH OR DEVELOPMENT

This investigation was made with United States government support awarded by the following agencies:
USDA Grant Number: 96-35500-3172

CROSS-REFERENCE TO RELATED APPLICATIONS

Not applicable.

BACKGROUND OF THE INVENTION

Within the United States, ongoing research is directed toward developing alternative energy sources to reduce our dependence on foreign oil and nonrenewable energy. The use of ethanol as a fuel has become increasingly prevalent in recent years. The current domestic use of ethanol in transportation fuels is about 1.2 billion gallons annually. In the U.S., the majority of ethanol is obtained from the fermentation of cornstarch. Projections made by the Department of Energy indicate that by the year 2020, annual ethanol usage in fuels will have increased dramatically to an estimated 20 billion gallons. This greatly exceeds what can be economically produced from cornstarch.

In order to meet the increased demand for ethanol, it will be necessary to ferment sugars from other biomass. Biomass refers to materials such as agricultural wastes, corn hulls, corncobs, cellulosic materials and the like. Biomass from most of these sources contains xylose at a concentration of up to about 25–30% of the total dry weight. The D-xylose content of hardwood species and herbaceous angiosperms is about 17% and 31% of the total dry weight, respectively. Because agricultural residues, pulping wastes, and fast-growing hardwood species have a high xylose content, the potential economic and ecologic benefits of converting xylose in these renewable materials are significant. In order for biomass conversion to be economically feasible, a practical, large-scale use must be found for xylose.

Biomass conversion employs microorganisms that serve as biocatalysts to convert cellulosic materials into usable end products such as ethanol. Efficient biomass conversion in large-scale industrial applications requires a microorganism that can tolerate high sugar and ethanol concentrations, and which is able to ferment multiple sugars simultaneously.

The pentoses D-xylose and L-arabinose are among the most difficult sugars in biomass to metabolize. Bacteria can ferment pentoses to ethanol and other co-products, and bacteria with improved ethanol production from pentose sugars have been genetically engineered. However, these bacteria are sensitive to low pH and high concentrations of ethanol, their use in fermentations is associated with co-product formation, and the level of ethanol produced remains too low to make the use of these bacteria in large-scale ethanol production be economically feasible.

In general, industrial producers of ethanol strongly favor the use of yeast as biocatalysts, because yeast fermentations are relatively resistant to contamination, are relatively insensitive to low pH and ethanol, and are easier to handle in large-scale processing. Many different yeast species use xylose respiratively, but only a few species use xylose fermentatively. Fermentation of xylose to ethanol by wild type xylose-fermenting yeast species occurs slowly and results in low yields, relative to fermentation rates and ethanol yields that are obtained with conventional yeasts in glucose fermentations. In order to improve the cost effectiveness of xylose fermentation, it is necessary to increase the rate of fermentation and the ethanol yields obtained.

The most commonly used yeast in industrial applications is *Saccharomyces cerevisiae*. Although *S. cerevisiae* is unable to grow on or ferment xylose, it was reported that homogenates of *S. cerevisiae* could readily ferment D-ribulose-5-phosphate to ethanol, and that it could also convert D-xylulose-5-phosphate to a lesser extent (Dickens, 1938). Efforts to create strains of *S. cerevisiae* with enhanced xylose fermentation by introducing genes capable of converting xylose to metabolites fermentable by *S. cerevisiae* have been largely unsuccessful (Ueng et al., 1985; Chan et al., 1989; Amore et al., 1989; Sarthy et al., 1987; Toivari et al., 1996).

*Pichia stipitis* is a yeast species that is able to ferment xylose to produce ethanol. In *P. stipitis*, fermentative and respirative metabolism co-exist to support cell growth and the conversion of sugar to ethanol (Ligthelm, 1988). *P. stipitis* differs significantly from the glucose-fermenting yeast *S. cerevisiae* in its ability to produce ethanol from xylose. It is known that *P. stipitis* requires a well-controlled low level of oxygen to reach maximum rate of ethanol production. In 1996, Passoth et al. first observed a peculiar pattern of respiration in *P. stipitis*. After the cells of *P. stipitis* were transferred from aerobic to oxygen-limited conditions, no decrease in the respiration capacity was observed. In addition, there was no increase in the respirative quotient ($CO_2$ production/$O_2$ consumption), and no change in the level of a key respiratory enzyme, pyruvate dehydrogenase. Moreover, respiratory activity was not repressed in the presence of fermentable sugars or low oxygen tension. In a survey of alternative pathways present in Crabtree-positive and -negative species, Jeppsson et al. (1995) reported that *P. stipitis* has an alternative respiratory pathway that is resistant to cyanide or antimycin A, but is sensitive to salicyl hydroxymate (SHAM). The pathway is believed to include a SHAM-sensitive terminal oxidase (STO). Jeppsson et al. hypothesized that the STO pathway would serve as a redox sink to avoid the accumulation of xylitol in *P. stipitis*.

Although STO respiration was discovered 70 years ago (Keilin, 1929), the physiological roles and the functional components of this pathway remain unclear. STO respiration has been widely reported from higher plants (for review, Douce and Neuburger, 1989; Vanlerberghe and McIntosh, 1997), fungi (Lambowitz and Slayman, 1971; Downie and Garland, 1973), and yeasts (Lloyd and Edwards, 1977). The STO pathway branches from the conventional cytochrome pathway at the level of ubiquinone, just before cytochrome b (Seidow, 1980; Storey, 1976), where electrons are directly donated to Sto to reduce molecular oxygen to water. Sto is unable to translocate protons (Moore and Rich, 1985), thus it by-passes two out of the three energy-generating sites in plants. Therefore, it is considered as an energy-wasting pathway. Most of the current information concerning biochemical and regulatory aspects of the pathway has been obtained from the studies in plant Sto proteins. Because this protein is tightly associated with the mitochondrial inner membrane, no pure forms have been obtained as yet for characterization studies of the metal center and kinetics. Moreover, the plant Sto proteins lose activity when they are solubilized. These difficulties have hindered progress in understanding the physiological roles of the STO pathway.

Research involving the identification and characterization of STO protein and its role in *P. stipitis* was undertaken in our laboratory. The information that resulted from these efforts has allowed us to develop genetically engineered, xylose-fermenting yeast strains with enhanced ethanol production from xylose.

BRIEF SUMMARY OF THE INVENTION

One aspect of the present invention is an isolated polynucleotide comprising a sequence encoding the *Pichia stipitis* SHAM-sensitive terminal oxidase of SEQ ID NO:26. Preferably, the isolated polynucleotide of the present invention is an isolated DNA molecule comprising the sequence of SEQ ID NO:25.

In another aspect, the present invention includes a vector comprising a polynucleotide comprising a sequence encoding *Pichia stipitis* SHAM-sensitive terminal oxidase, SEQ ID NO:26.

The present invention provides a genetic construct comprising a sequence encoding the *Pichia stipitis* SHAM-sensitive terminal oxidase of SEQ ID NO:26 operably connected to a promoter functional in yeast.

The present invention provides a xylose-fermenting mutant of a yeast or fungal species, the mutant having reduced SHAM-sensitive terminal oxidase relative to the levels of SHAM-sensitive terminal oxidase in the parent strain from which the mutant was derived, wherein the species is selected from the group consisting of *Pichia stipitis*, Group I species and Group II species, wherein Group I species natively comprise a cytochrome pathway and a SHAM-sensitive pathway, and wherein Group II species natively comprise a cytochrome pathway, an antimycin A- and SHAM-insensitive pathway, and a SHAM-sensitive pathway. Preferably, the mutant yeast strain is a *P. stipitis* mutant.

In one embodiment, the mutant xylose-fermenting yeast is a *P. stipitis* SHAM-sensitive terminal oxidase disruptant. Preferably, the *P. stipitis* SHAM-sensitive terminal oxidase disruptant is derived from FPL-UC7 (NRRL 21448). More preferably still, the *P. stipitis* SHAM-sensitive terminal oxidase disruptant is FPL-Shi 31 (NRRL Y-30230).

In an alternative embodiment, the mutant xylose-fermenting yeast comprises a construct expressing SHAM-sensitive terminal oxidase antisense mRNA.

A further aspect of the invention is a method for producing ethanol from the fermentation of xylose comprising the steps of culturing a mutant of xylose-fermenting yeast in a xylose-containing medium under suitable conditions for a period of time sufficient to allow fermentation of xylose to ethanol, the mutant yeast having reduced SHAM-sensitive terminal oxidase relative to the wild type parental strain from which the mutant is derived.

The present invention includes a recombinant yeast comprising a sequence encoding the *Pichia stipitis* SHAM-sensitive terminal oxidase of SEQ ID NO:26, the coding sequence operably connected to a promoter functional in yeast, the yeast belonging to a species selected from the group consisting of *Saccharomyces cerevisiae, Saccharomyces carlsbergensis, Saccharomyces byanus, Saccharomyces delbrueckii, Saccharomyces diastaticus, Saccharomyces sake, Saccharomyces thermotolerans, Saccharomyces urvarum* and Group III species, wherein the recombinant yeast expresses SHAM-sensitive terminal oxidase and wherein expression of the SHAM-sensitive terminal oxidase is correlated with cyanide-resistant respiration, the yeast species natively comprising an antimycin A-insensitive pathway and a cytochrome pathway.

It is an advantage that the mutant xylose-fermenting yeast of the present invention ferments xylose at an increased rate, relative to the parent strain having wild-type levels of SHAM-sensitive terminal oxidase.

Other advantages and features of the present invention will become apparent upon review of the specification.

DETAILED DESCRIPTION OF THE INVENTION

Figure 1:
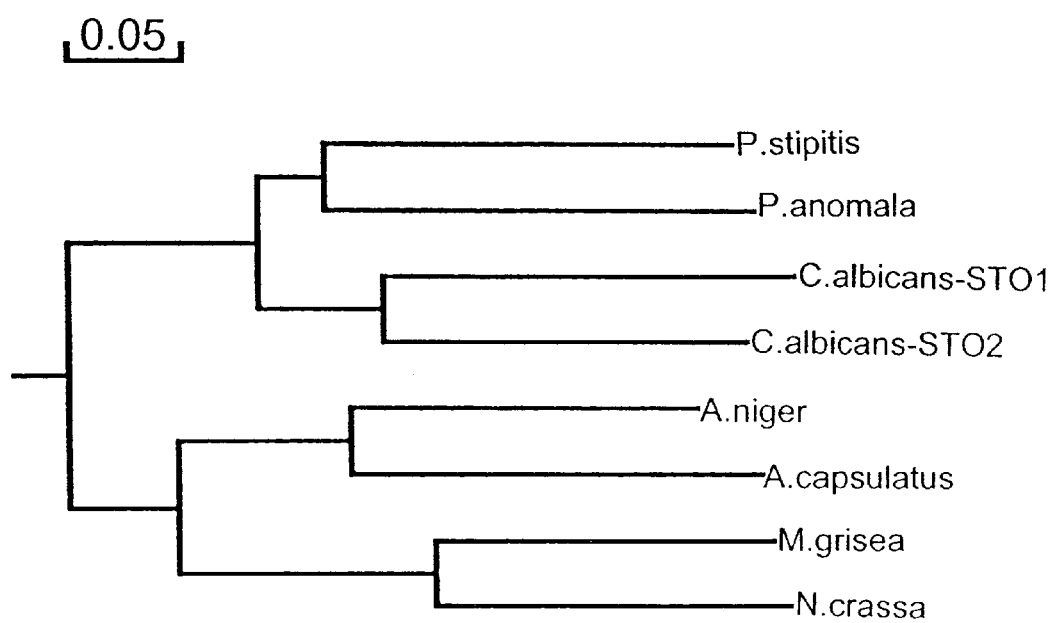
FIG. 1 shows the phylogenetic relationship of PsSto to Sto proteins from seven other yeast and fungi.

*Pichia stipitis* is a crabtree-negative yeast with oxidative and fermentative metabolism coexisting, which include a cytochrome pathway and a cyanide or antimycin A resistant, SHAM-sensitive pathway. We previously discovered that disruption of the cytochrome pathway in *P. stipitis* results in increased xylose fermentation (U.S. Pat. No. 6,071,729, which is incorporated by reference in its entirety).

As reported herein, we have identified, cloned and sequenced a coding sequence for SHAM-sensitive terminal oxidase from *P. stipitis*. The gene is designated PsSTO1 for *Pichia stipitis* SHAM-sensitive terminal oxidase. Using the PsSTO1 coding sequence, a disruption and an expression vector were developed.

The disruption cassette was used to create a mutant of *Pichia stipitis* in FPL-UC7, which contains the PsSTO1 gene and has wild type levels of PsSto. The PsSTO1 disruptant mutant of *Pichia stipitis* was characterized as described in detail in the Examples. Briefly, the mutant grown on xylose showed faster xylose utilization, exhibited higher volume production of ethanol, and had reduced cell growth relative to the parent strain from which the mutant was derived. Faster xylose utilization, increased ethanol production, and reduced cell growth are all desirable properties for a yeast used in industrial fermentations.

A genetic construct comprising the PsSTO1 gene operably connected to a promoter functional in yeast was introduced into *Saccharomyces cerevisiae* and expression of PsSto protein was obtained. It if of interest to note that the respiration rate of transformed *S. cerevisiae* increased relative to that of a control yeast. Respiration was resistant to KCN, which suggests the expression of PsSTO1 can impart functional SHAM-sensitive respiration in *S. cerevisiae*.

To date, efforts to enhance xylose fermentation to ethanol by *S. cerevisiae* by introducing into the yeast xylose fermenting enzymes (e.g., xylose reductase or xylitol dehydrogenase) have proven ineffective. At low oxygen levels, recombinant *S. cerevisiae* with a wild type cytochrome respiratory system converts xylose into xylitol. Instead of being converted to ethanol, xylitol accumulates because of the cofactor imbalance of the first two step enzymes in the engineered xylose pathway. In addition, $S.$ $cerevisiae$ does have transhydrogenases to use NADPH to regenerate $NAD^+$. We hypothesized that by introducing the Sto protein into $S.$ $cerevisiae$, it may be possible to confer cyanide resistant respiration to promote regeneration of $NAD^+$ in $S.$ $cerevisiae$.

We have transformed $S.$ $cerevisiae$ with a PsSTO1 gene under control of a constituitive ScGAPDH promoter and found that transformants have increased respiration that is resistant to cyanide. Any promoter that is functional in yeast may be used in place of the ScGAPDH promoter to allow expression of a heterologous PsSTO gene in yeast. It is reasonably expected that $S.$ $cerevisiae$ mutants expressing Sto proteins with the combination of xylose reductase and xylitol dehydrogenase will have enhanced ethanol production from biomass. Therefore, the $S.$ $cerevisiae$ mutants of the present invention will make good targets for developing genetically engineered yeast with heterologous enzymes involved in xylose fermentation.

It is expected that other commercially important yeast that are closely related to $S.$ $cerevisiae$ may also be genetically engineered to express Sto proteins. Suitable yeast species include, but are not limited to, $Saccharomyces$ $carlsbergensis$, $Saccharomyces$ $byanus$, $Saccharomyces$ $delbrueckii$, $Saccharomyces$ $diastaticus$, $Saccharomyces$ $sake$, $Saccharomyces$ $thermotolerans$, and $Saccharomyces$ $urvarum$.

The present invention provides a mutant xylose-fermenting yeast strain that is characterized by reduced expression of a functional SHAM-sensitive terminal oxidase. The mutant yeast of the present invention has been found to ferment xylose to produce ethanol at a higher rate than the parent strain, which has wild-type levels of SHAM-sensitive terminal oxidase.

Preferably, the mutant yeast strains of the present invention have volumetric ethanol production rates that are about 20% or more higher than that of the corresponding parent strain having wild type levels of SHAM-sensitive terminal oxidase.

In a preferred embodiment, the mutant yeast of the present invention is a SHAM-sensitive terminal oxidase disruptant mutant. By a "SHAM-sensitive terminal oxidase disruptant mutant," it is meant a mutant in which a part or all of the functional SHAM-sensitive terminal oxidase gene natively present in the parent strain is removed or replaced with DNA, the expression of which does not result in an expression product having SHAM-sensitive terminal oxidase activity.

In an alternative embodiment, expression of SHAM-sensitive terminal oxidase may be down-regulated through the use of an anti-sense construct in which part or all of the antisense strand coding for the SHAM-sensitive terminal oxidase is expressed under the regulation of a promoter that responds to diminished oxygen. In this embodiment, the antisense mRNA for SHAM-sensitive terminal oxidase is expressed under oxygen limiting conditions, and thereby inhibits translation of SHAM-sensitive terminal oxidase transcript. Using the sequence information disclosed herein, one of ordinary skill in the art could construct a vector expressing antisense RNA.

By "wild-type yeast," it is meant a xylose-fermenting yeast strain with normal or wild-type levels of functional SHAM-sensitive terminal oxidase from which the mutant strain of the present invention is derived. In certain cases, the "wild-type yeast" as defined herein may include mutagenized yeast. For example, the $P.$ $stipitis$ strain FPL-UC7, from which the PsSTO1 disruptant FPL-Shi31 was developed, is itself a mutated yeast strain. However, FPL-UC7 is also a wild-type yeast, as defined herein, because it is a xylose-fermenting yeast with normal levels of functional SHAM-sensitive terminal oxidase used to develop a mutant yeast strain of the present invention.

As described in detail in the Examples, a disruption cassette comprising a 1.4-kb PsURA3 fragment inserted into the PsSTO1 gene was introduced by site-specific integration into the genome of $P.$ $stipitis$ FPL-UC7 (Lu, et al. 1998b), a ura3 auxotroph. A resultant disruptant strain, designated FPL-Shi31, was obtained and characterized as detailed below. The $P.$ $stipitis$ strain FPL-Shi31 was deposited at the ARS Patent Culture Collection in Peoria, Ill. on Oct. 20, 1999 under the Budapest Treaty and was assigned accession number NRRL Y-30230. It is reasonably expected that similar stol-Δ disruptants of $P.$ $stipitis$ may be obtained using a disruption cassette comprising larger or smaller portions of the 5' and 3' regions of the PsSTO1 gene or its flanking regions.

In addition to FPL-Shi31, other sto1-Δ disruptant mutants can readily be obtained using FPL-UC7 (NRRL Y-21448) or $P.$ $stipitis$ FPL-PLU20 (Lu et al., 1998; Cho and Jeffries, 1999), as the progenitor. The $P.$ $stipitis$ strain FPR-PLU20 was deposited at the ARS Patent Culture Collection in Peoria, Ill. on Mar. 30, 1998 under the Budapest Treaty and was assigned accession number NRRL Y-21970.

Several yeast and fungal species in addition to $P.$ $stipitis$ are known to employ more than one respiratory pathway. These species can be assigned to one of four groups: Group I (a cytochrome pathway and SHAM sensitive pathway); Group II (a cytochrome pathway, an antimycin A- and SHAM-insensitive pathway, and a SHAM-sensitive pathway); Group III (an antimycin A-insensitive pathway and a cytochrome pathway); and Group IV (cytochrome c pathway). Group I includes $Pichia$ $stipitis$, $Hansenula$ $anomala$, $Hansenula$ $California$, $Schwanniomyces$ $castellii$, $Aspergillus$ $niger$, and $Neurospora$ $crassa$. Group II includes $Hansenula$ $saturnus$ and $Endomycopsis$ $capsularis$. Group III includes $Schizosaccharomyces$ $pombe$, $Candida$ $utilis$, $Candida$ $parapilosis$, and $Kluyveromyces$ $lactis$. Group IV includes $Hansenula$ $glucozyma$.

It is anticipated that a mutant having reduced expression of functional SHAM-sensitive terminal oxidase may be easily obtained from any member of Group I or II yeast using standard molecular biology techniques and the teachings set forth herein. For example, one wishing to obtain such a mutant could isolate the STO gene from the target species, construct a disruption cassette having a selectable marker such as URA3, transform a sensitive strain (e.g., a ura3 auxotrophic strain) with the cassette, and select for putative transformants on selection medium (e.g., medium lacking uracil). Putative disruptants may be confirmed by PCR amplification as described in the Examples.

It is reasonably expected that, in addition to expressing SHAM-sensitive terminal oxidase in $S.$ $cerevisiae$, expression of SHA-sensitive terminal oxidase and cyanide-resistant respiration may be achieved by introducing a heterologous SHAM-sensitive terminal oxidase gene operably connected to a promoter expressible in yeast into $Saccharomyces$ $carlsbergensis$, $Saccharomyces$ $byanus$, $Saccharomyces$ $delbrueckii$, $Saccharomyces$ $diastaticus$, $Saccharomyces$ $sake$, $Saccharomyces$ $thermotolerans$, and $Saccharomyces$ $urvarum$ or Group III yeast using the teachings of the present invention and standard molecular biological techniques.

In another aspect, the present invention provides a method of fermenting xylose in a xylose-containing material to produce ethanol using the mutant yeast of the invention as a biocatalyst. Preferably, the mutant yeast is recovered after the xylose in the medium is fermented to ethanol and used in subsequent fermentations.

By "xylose-containing material," it is meant any medium comprising xylose, whether liquid or solid. Suitable xylose-containing materials include, but are not limited to, hydrolysates of polysaccharide or lignocellulosic biomass such as corn hulls, wood, paper, agricultural by-products, and the like.

By a "hydrolysate" as used herein, it is meant a polysaccharide that has been depolymerized through the addition of water to form mono and oligosaccharides. Hydrolysates may be produced by enzymatic or acid hydrolysis of the polysaccharide-containing material, or by an other suitable means.

Preferably, the mutant yeast strain is able to grow under conditions similar to those found in industrial sources of xylose. The method of the present invention would be most economical when the xylose-containing material can be inoculated with the mutant yeast without excessive manipulation. By way of example, the pulping industry generates large amounts of cellulosic waste. Saccharification of the cellulose by acid hydrolysis yields hexoses and pentoses that can be used in fermentation reactions. However, the hydrolysate or sulfite liquor contains high concentrations of sulfite and phenolic inhibitors naturally present in the wood which inhibit or prevent the growth of most organisms. Passaging of the yeast selects for yeast that are better able to grow in the presence of sulfite or phenolic inhibitors.

It is expected that mutant yeast strains of the present invention may be further manipulated to achieve other desirable characteristics, or even higher specific ethanol yields. For example, selection of mutant yeast strains by passaging the mutant yeast strains of the present invention on medium containing hydrolysate may result in improved yeast with enhanced fermentation rates.

The sequence of the deduced amino acid sequence of the putative protein encoded by the *Pichia stipitis* STO1 gene is provided in SEQ ID NO:26. The sequence of the STO1 gene isolated from *Pichia stipitis* is shown in SEQ ID NO:25. It is understood that the sequence encoding the STO to be expressed or used in the construction of a disruption cassette can have a sequence with minor variations, substitutions, additions or deletions relative to the sequence isolated from *P. stipitis* shown in SEQ ID N:25.

With respect to expression of the STO gene, it is well understood among those of ordinary skill in the art that certain changes in nucleic acid sequence make little or no difference to the overall function of the protein or peptide encoded by the sequence. Due to the degeneracy of the genetic code, particularly in the third position of codons, changes in the nucleic acid sequence may not result in a different amino acid being specified by that codon. Changes that result in an amino acid substitution may have little or no effect on the three dimensional structure or function of the encoded protein or peptide. In addition, changes that result in insertions or deletions of amino acids may also be acceptable.

Similarly, slight variations in the sequence of the STO gene are expected to be suitable for the use of the STO gene in the development of a disruptant mutant. It is important that there is a sufficiently high degree of complementarity between the STO gene used in constructing the disruption cassette and that of the target host so as to permit efficient, site specific recombination to occur.

The following non limiting examples are intended to be purely illustrative.

EXAMPLES

I. Methods and Materials

A. Microbial strains and maintenance

Microbial strains used in this study are listed in Table 1. *P. stipitis* strains were maintained or cultivated in YNB minimal medium containing 1.7 g $L^{-1}$ yeast nitrogen base without amino acids (YNB; Difco), 5 g $L^{-1}$ ammonium sulfate, and 20 g $L^{-1}$ glucose. For yeast transformations, yeast host strains were grown in YPD medium consisting of yeast extract, 10 g·$L^{-1}$, peptone, 20 g·$L^{-1}$, and glucose, 20 g·$L^{-1}$. For cultivation of ura3 and leu2 auxotrophs, media were supplemented with 20 mg·$L^{-1}$ of uridine or leucine, respectively. For other growth or fermentation experiments, yeast strains were normally grown in YNBUP medium containing 1.7 g·$L^{-1}$ yeast nitrogen base without amino acids, 2.27 g·$L^{-1}$ urea, 6.56 g·$L^{-1}$ peptone, and sugar (2–4%). Yeast strains were cultivated at 30° C. *E. coli* was cultivated at 37° C. in Luria-Bertani medium supplemented with 100 mg·$L^{-1}$ ampicillin or kanamycin when required.

TABLE 1

Microbial strains

| Strain | Genotype (NRRL number) | Reference or source |
|---|---|---|
| *P. stipitis* | Wild-type (NRRL Y-1145) | Centraalbureau voor Schimmelcultures (Delft, The Netherlands) |
| FPL-UC7 | ura3-3 (NRRL Y-21448) | Lu et al., 1998 |
| FPL-Shi21 | cyc1::ura3 (NRRL Y-21971) | Shi et al., 1999 |
| FPL-Shi31 | sto1::ura3 (NRRL Y-21971) | This work |
| FPL-Shi41 | sto1::ura3 | This work |
| FPL-PLU5 | ura3-3, leu2Δ | Lu, et al., 1998 |
| *S. cerevisiae* | | |
| 679α | MATαtrp1-1 | Dr. Culbertson (Univ. of Wisconsin, Madison, WI) |
| 679α (pNQ32) | Contains expression cassette of PsSTO1 | This work |
| 679α (pYPR2831) | Contains empty vector without PsSTO1 | This work |
| B06748 | MATα can1-100 cyc1-783 cyc1::lacZ) cyc7::CYH2+cyh2 his3-Δ1 leu2-3 112, trp1-289 ura3-52 | Holzschu et al., 1989 |
| B06748 (pNQ32) | Contains expression cassette of PsSTO1 | This work |
| B06748 (pYPR2831) | Contains empty vector without PsSTO1 | This work |
| *Escherichia coli* | | |
| DH5α | F⁻ recA1 endA1 hsdR17 ($r_K^-$, $m_K^+$) supE44 thi-1 gyrA relA1 | Life Technologies |
| TOP10 | F⁻ mcrA Δ (mmr⁻ hsdRMS-mcrBC) Φ80lacZΔM15 ΔlacX74 recA deoR ara D139 Δ (ara-leu) 7697 galU galK rpsL (Str$^R$) endA1 nupG | Invitrogen |

B. Enzmes, primers and chemicals

Restriction enzymes, DNA modification enzymes and molecular reagents were obtained from New England Biolabs, Promega, Strategene and Roche Biochemicals. Reaction conditions were as recommended by the suppliers.

All general chemicals were purchased from Sigma and Fisher. All DNA preps were performed using Qiaprep Spin columns from Qiagen. Zymolyase 20T was purchased from ICN while Novozyme234 was purchased from Sigma. Oligo primers were synthesized by Sigma-Genosys. The oligonucleotides used in this study are listed in Table 2; vectors are listed in Table 3.

TABLE 2

Oligonucleotides

| Template | Primer number and sequence |
|---|---|
| CBS 6054 genomic DNA | 1:5ATITTCCTYGAATCYRTYGCYG-GIGTYCCWGG-3'<br>2:5'ACRGCYTCYTCYTCIARGTAD-CCRACGAATCTGTG-3' |
| Linear fragment | 3: 5'-GTAATACGACTATAGGGC-3' (AP1)<br>4: 5'-ACTATAGGGCACGCGTGGT-3' (AP2) |
| libraries of CBS 6054 | 5: 5'-CCGTTGCTTCCTTCATCAGACAC-TTGCAT-3'<br>6: 5'-GGTGTATTCTGCAACTTGTTCTT-CTTGT-3'<br>7:5'-AAGAATGCAAGTGTCTGATGARGAAG-GAAGCAA-3'<br>8: 5'-GAACAAGAAGAACAAGTTGCAGA-ATACAC-3'<br>9: 5'-GGCTCGTCTTTACGTCTTCGCAT-CTCAT-3' |
| PsSTO1 (3 kb) | 10: 5'-GCATGTGAAGACTTGAACGGGTT-GACTT-3'<br>11: 5'-CCATCGATGGGAGCCGTTGTCTG-AGAAG-3' |
| PsURA3 (1.4 kb) | 12: 5'-CCATCGATGGAATAGGCCTCTGC-TTGT-3'<br>13: 5'-ATGCTTCTGTGCAGACTACAAGA-GCC-3' |
| PsSTO1 coding region | |
| (1.1 kb) | 14: 5'-TTACAATTTCAATTCTTCCTTCT-CCC-3' |
| PsLEU2 (1.6 kb) | 15: 5'-GGCATGACTAACCAAAGTGAA-3'<br>16: 5'-CGTTCGCTCTTGTGAGAGCATT-3'<br>17: 5'-CGGGATCCGAGCTGTCTCATGTC-CCTTACAA-3' |
| PSCYCI 5'flanking | |
| region (1 kb) | 18: 5'-CGGGATCCACCTGGGATGTACTT-CTTTGGGTT-3'<br>19:5'-CCGCTCGAGCCAGCATAGAGTGAACG-AAACCAC-3' |
| PsCYC1 3'flanking | |
| region (0.8 kb) | 20: 5'-CCGCTCGAGCAGGGAGCTTTAGA-CCAGCATGGT'-3' |
| PsCYC1 coding region | 21: 5'-ATGCCAGCTCCATTCGAAAGGG-3' |
| (0.3 kb) | 22: 5'-TTACTTGGTGGCGGAAGCCAAG-3'<br>23: 5'-CCGCTCGAGCGGATGCTTCTGTG-CAGACTACA-3' |
| PsSTO1 coding region | |
| (1.1 kb) | 24: 5'-CCGCTCGAGCGGTTACAATTTCA-ATTCTTCCTTC-3' |

TABLE 3

Vectors and plasmids

| Plasmid | Relevant characteristics | Reference |
|---|---|---|
| PCR2.1 TOPO | Cloning vector | Invitrogen |
| PCR Blunt II-TOPO | Cloning vector | Invitrogen |
| pNQ28 | Contains the 293 bp PsSTO1 | Thiswork |
| pNQ30 | Contains full length (3.0 kb) PsSTO1 | This work |
| pNQ31 | Contains the PsSTO1 disruption cassette | This work |
| pYPR2831 | Contains ScGAPD promoter and terminator | Horiuchi et al., 1990 |
| pNQ32 | Contains the expression cassette of PsSTO1 in pYPR2831 | This work |
| pNQ35 | Contains 0.9 kb PsACT1 gene | This work |
| pNQ38 | Contains RT-PCR products of PsSTO1 | This work |
| pNQ37 | Contains PsLEU2 cassette | This work |
| pNQ39 | Contains PsLEU2 cassette fused to PsCYCZ 5' flanking region | This work |
| pNQ41 | Contains PsCYC1 disruption cassette using PsLEU2 | This work |

C. DNA sequencing

Sequencing of all DNA clones was performed by using a 371 ABI automated sequencer (Perkin-Elmer). DNA sequence analysis was conducted by using the Genetics Computer Group sequence analysis software package and DNAMAN (Lynnon BioSoft). Phylogenetic trees were drawn according to the neighbor-joining method (Kimura, 1983).

D. Genome walking to clone the alternative oxidase

Two highly conserved regions of the six fungal alternative oxdiases: IFLES(I/V)AGVPGMV (SEQ ID NO:27 and SEQ ID NO:28, respectively) and HRFVGYLEEEAV (SEQ ID NO:29), were selected to design two degenerate oligos. Primer 1 and 2 (SEQ ID NO: 1 and SEQ ID NO:2, respectively) were used to amplify a 293-bp region of PsSTO1 from *P. stipitis* wild-type CBS 6054 by Pfu DNA polymerase (Strategene). The PCR reaction was carried out at 95° C. for 5 min as the initial cycle, followed by 36 cycles of 95° C. for 60 s, 55° C. for 60 s and 72° C. for 90 s. The final extension time was 15 min at 72° C. One μL PCR products were directly cloned into the PCR2.1-TOPO vector (Invitrogen) to create pNQ28. The 293-bp fragment was sequenced and compared to the consensus of the fungal alternative oxidase genes. This region became the starting point for genome walking to clone the entire gene.

The Universal Genome Walker Kit (Clonetech) was used to clone PsSTO1. One jig of genome DNA from wild-type CBS 6054 was used to construct five individual linear fragment libraries by 5 blunt-end enzymes supplied in the kit. The blunt-ended linear fragments were ligated to the adapters provided by the manufacturer. Gene-specific primers were designed based on the sequence of the 293-bp amplified region to allow "walking" in each direction. The two adapter specific primers (3 and 4) were supplied by the manufacturer. For the 3' end walking, primers 3 and 5 (SEQ ID NO: 3 and SEQ ID NO:5, respectively) were used to amplify the primary PCR products, while primers 4 and 6 (SEQ ID NO:4 and SEQ ID NO:6, respectively) were used for the secondary PCR using the first round of PCR products as templates. For the 5' end walking, primers 3 and 7 (SEQ ID NO:3 and SEQ ID NO:7, respectively) were used for the primary PCR, while primers 4 and 8 (SEQ ID NO:4 and SEQ ID NO:8, respectively) were used for the second round.

The Advantage PCR kit (Clontech) was used in all the PCR reactions for walking. The PCR conditions were as recommended by the manufacturer's manual. The secondary PCR products were directly cloned into the PCR2.1-TOPO vector for DNA sequencing. After obtaining the sequences, primers 9 and 10 (SEQ ID NO:9 and SEQ ID NO:10, respectively) were used to amplify a 3-kb PsSTO1 fragment by using Pfu DNA polymerase (Strategene). This fragment, which contained 1 kb of each flanking region and the coding region, was cloned into the PCR-BluntII-TOPO vector (Invitrogen) as pNQ30. This 3-kb clone was fully sequenced as the final deposited data.

E. Isolation of MRNA and RT-PCR

Cells of CBS 6054 grown under fully aerobic conditions (OD600<2) on YNB-xylose (2%) were used to isolate total RNA. Under this condition, no ethanol was formed (Shi et al., 1999). mRNA was extracted using a Dynabeads mRNA Direct Kit (Dynal). 100 $\mu$L cells were mixed with 1 mL lysis buffer and Dynabead Oligo (dT)25 for 5 min. The mRNA was separated by a Magnetic Separation Stand (Promega) and washed twice with the washing buffer. The mRNA was eluted at 65 °C. and stored at $-80$° C. for future uses. Reverse transcription PCR (RT-PCR) was performed by using a Super Script One-Step RT-PCR System (Life Technologies). The reaction volume was 50 $\mu$L containing 0.3 $\mu$g mRNA, 0.2 $\mu$M each primer, 25 $\mu$L 2× reaction mix, 1 $\mu$L Super Script RT/Taq DNA polymerase mix. cDNA was synthesized at 50° C. for 3 min and denatured at 94° C. for 2 min. The nRT-PCR was carried out by running a program consisting of 40 cycles: 94° C. for 15 s, 55° C. for 30 s and 72° C. for 80 s. The final RT-PCR reaction was terminated with 1 cycle of 72° C. for 10 min. The primers for RT-PCR of PsSTO1 were SEQ ID NO:11 and SEQ ID NO:12.

F. Construction of the single stol-Δknockout stain

A one-step gene replacement method was employed to disrupt the PsSTO1 gene in FPL-UC7 (Lu et al., 1998). A 1.4-kb PsURA3 fragment was amplified from pVY2 (Yang et al., 1994) using Pfu DNA polymerase by primers 13 and 14, (SEQ ID NO:13 and SEQ ID NO:14, respectively) with a ClaI site at each end. The PCR conditions were the same as described in Shi and Jeffries (1998). This fragment was digested with ClaI, and sub-cloned into the ClaI site of the PsSTO1 coding region in pNQ30 to create pNQ31.

G. Yeast transformation

The disruption cassette was liberated from pNQ31 by NdeI and EcoRI, and used to transform FPL-UC7. This cassette was also used to transform another P. stipitis host, PLU5, which has two selectable markers (Lu et al., 1998). REMI transformation (SÝnchez et al., 1998) was carried out by using the EZ-transformation kit (Bio101). Putative stol-Δ colonies from FPL-UC7 or FPL-PLU5 were picked after 2–3 days on YNB-glucose (2%) minimum medium without uridine.

H. Screening of putative stol-Δ disruptants

Two $\mu$L of the yeast cells were lysed by using a Yeast Whole Cell Lysis Kit (Bio101) at 37° C. for 1 h. The resulting lysate was mixed with 200 $\mu$M dNTPs, 10 $\mu$M each primer, 10×PCR buffer, 1.5 mM MgCl$_2$ to 99 $\mu$L volume, and heated at 95° C. for 15 min. Five units of Taq DNA polymerase (Roche) were added to the mixture, and the PCR reaction was run with 40 cycles of: 95° C. for 1 min, 50° C. for 1 min And 72° C. for 1 min. The PCR reaction was terminated with 4 min of final extension at 72° C. Primers 11 and 12 (SEQ ID NO:11 and SEQ ID NO:12) were used to screen the putative disruptants. The single knockout strain from FPL-UC7 was named FPL-Shi31while the single knockout from FPL-PLU5 was named FPL-Shi41.

I. Construction of a double knockout (sto1-Δ, cyc1-Δ) strain

In order to obtain a double knockout strain using FPL-Shi41, a new PsCYC1 disruption cassette was constructed. A PsLEU2 cassette was amplified by primers 15 and 16 (SEQ ID NO:15 and SEQ ID NO:16, respectively), and the fragment was sub cloned in the BluntII-TOPO vector to make pNQ37. A 1-kb 5' flanking region of PsCYC1 was amplified by primers 17 and 18 (SEQ ID NO:17 and SEQ ID NO:18, respectively) with a BamHI site at each end. This fragment was cut with BamHI and cloned into the BamHI site of pNQ37 to create pNQ39. A 0.8-kb 3' flanking region of PsCYC1 was amplified by primers 19 and 20 (SEQ ID NO:19 and SEQ ID NO:20, respectively) with a XhoI site at each end. This fragment was cut with XhoI and cloned into the XhoI site of pNQ39 as pNQ41. The resultant disruption cassette was linearized by NdeI and NcoI, and used to transform FPL-Shi41. The putative double knockout colonies were selected on YNB-glucose minimum medium without uridine and leucine. The putative disruptant colonies were screened by colony PCR using primers 21 and 22 (SEQ ID NO:21 and SEQ ID NO:22, respectively).

J. Mitochondrial isolation and protein analysis

P. stipitis cells were grown overnight in 25 mL sugar-limited medium (yeast extract, 3 g·L$^{-1}$, malt extract, 3 g L$^{-1}$, xylose, g L$^{-1}$) in a 125-mL baffled flask (Guvinden, 1995). The flask was shaken at 160 rpm at 30° C. The next day, 15 mL of the overnight culture was used to inoculate 500-mL fresh medium in a 2-L baffled flask. The culture was shaken at 160 rpm at 30° C. for 24 h. Mitochondria from P. stipitis were isolated mechanically as described by (Luttik et al., 1998) or by the sucrose gradient ultra centrifugation method (Defontaine et al., 1991; Querol and Barrio, 1990). For the mechanical method, 20 mg Zymolase 20T was used in 35 mL of buffer A containing 25 mM potassium phosphate, 1 mM MgCl$_2$, 1 mM EDTA (pH 7.5). For the sucrose gradient method, the cells harvested from of one liter cultures. The cells were treated with 0.5 mg·L$^{-1}$ Novozyme 234 in 5 mL of solution A containing 0.5 M sorbitol, 10 mM Tris-HCl (pH 7.5). Mitochondrial protein was released by using glass beads in a cell disruption buffer containing 100 mM sodium phosphate, 1 mM EDTA and 5 mM β-mercaptolethanol (Ciriacy, 1975). After vortexing three times for 1-min in a glass tube, the mixture was transferred to a new microfuge tube. The tube was spun down at 16,000 g for 2 min and the top layer was transferred to a new microfuge tube. Protein concentration was determined by the BCA protein assay system (Pierce). Fifteen $\mu$g mitochondrial protein was loaded on a 10–20% Tris-HCl reducing SDS-PAGE gradient gel (Biorad). After electrophoresis (40 min at 200 volts), the protein was transferred to a nylon membrane (Schleicher & Schuell). The blot was first hybridized with 1:100 dilution of a mouse monoclonal antibody raised against the Sto of Sauromatum guttatum (Elthon et al., 1989), then the blot was cross-reacted with an anti-mouse secondary antibody conjugated with an alkaline phosphatase at a 1:5000 dilution (Promega). The color was developed by the NBT/BCIP system (Promega).

K. Expression of PsSTO1 in S. cerevisiae

To express the PsSTO1 gene in S. cerevisiae, the coding region was amplified using Pfu DNA polymerase from CBS 6054 genomic DNA. Primers 23 and 24 (SEQ ID NO:23 and SEQ ID NO:24, respectively) were used, which contained a XhoI site at each end. The PCR conditions were described in Shi and Jeffries (1998). The amplified fragment was digested with XhoI, and cloned into the SalI site of an expression vector, pYPR2831 (Horiuchi et al., 1990) by using a Rapid DNA Ligation Kit (Roche). Thus, the PsSTO1 was driven by the constitutive glyceraldehyde phosphate dehydrogenase (GAPDH) promoter from S. cerevisiae, and terminated with the GAPDH terminator. The resultant clone was named as pNQ32, and 5 μg of the plamid DNA was used to transform two S. cerevisiae strains, 679α a gift from Dr. Michael Culbertson, University of Wisconsin, Madison, Wis.) and B06748 (Holzschu et al., 1989). The empty vector without the PsSTO1 was also used to transform as the control. Yeast transformation was carried out by using the EZ-transformation Kit (Bio101). Necessary amino acids were added when required for the growth of the control strains.

L. Analysis of the S. cerevisiae transformed with PsSTO1

Primers 13 and 14 (SEQ ID NO:13 and SEQ ID NO:14) were used to confirm the transformants carrying the PsSTO1 expression cassette. Transformants carrying the expression cassette were used for subsequent studies. For the 679α transformants bearing the pNQ32 or pYPR2831 plasmid, cells were grown in 500 mL fresh YNBUP medium containing 8% glucose. The cells were grown in 1-L flask and the flask was shaken at 30° C. at 140 rpm for 2 days. The cells were harvested and washed twice with 20 mM potassium phosphate buffer (pH 7.0) containing 5 mM magnesium chloride, and resuspended in 4.5 mL of the same buffer. Oxygen uptake rates were measured as described above and the assay substrate was 5mM ethanol.

For the B06748 transformants bearing the pNQ32 or pYPR2831 plasmid, a fermentation study was carried out instead of measuring respiration. The strains were first grown in 50 mL fresh YNBUP medium containing 2% glucose for three days at 30° C. The cells were shaken at 140 rpm in a 125-mL Erlenmeyer flask. The cells were harvested and washed with sterile water twice. Then the 3-day-grown cells were cultivated in fresh YNBUP medium at 30° C. in a 125-mL Erlenmeyer flask that was shaken at 140 rpm.

M. Dry weight determination and HPLC analysis

Cells were spun down at 16,000 g for 5 min, washed with water for three times, and desiccated in a 105° C. oven overnight. At least 2 to 3 replicate samples were used to determine dry weight. One optical density (OD) unit at λ=600 nm corresponds to 0.22 g FPL-UC7 and FPL-Shi31cells (dry weight) per liter, or 0.2 g FPL-Shi21 cells (dry weight) per liter. For analyzing fermentation end products, samples were drawn daily and the samples were spun at 16,000 g for 5 min. The supernatant solution was diluted 5 fold and subjected to high performance liquid chromatography(HPLC) analysis by using an ICSep-ION-300 column (CETAC Technologies). The column was operating at 60° C. with a 0.4 mL/min flow rate using 0.008 M sulfuric acid as the solvent. Glucose, xylose, xylitol and ethanol are eluted at 16.3 min, 17.5 min, 22.8 min and 34.8 min, respectively.

N. Cytochrome spectra studies

Strains of P. stipitis were grown in yeast extract medium containing 2% xylose, glucose or ethanol as the sole carbon source. The yeast cells were grown on the surface of a plate for three days as thin "lines" and examined by a spectroscope as described by Sherman et al. (1974). Low temperature (−196° C.) spectro-photometric recordings of the FPL-UC7 and FPL-Shi31 were performed with whole cells. The strains were grown on 1% yeast extract, 2% peptone, and 2% xylose at 30° C. for three days. The absorption spectra were recorded as previously described (Hickey et al., 1991).

O. Aerobic growth studies

P. stipitis cells were grown in 25 mL YNBUP medium containing either 2% glucose or 2% xylose in a 125-mL baffled flask. The flask was shaken at 140 rpm at 30° C. for 3 days. The cells were harvested and washed with sterile water twice. The culture was then used to inoculate a 25 mL fresh YNBUP medium containing either 2% glycerol or 2% ethanol in a 125-mL baffled flask. The flask was shaken at 140 rpm at 30° C. The starting cell density was 0.05 g L$^{-1}$. Samples were taken every 4 h to monitor growth by measuring the optical density at λ=600.

P. Shake-flask fermentation trial

Strains of FPL-Shi31, and FPL-UC7 were grown for 2 days under oxygen-limited conditions (Shi et al., 1999) in YNBUP medium containing 2% glucose or xylose. Cells were harvested and washed twice with sterile water. Cells were then used to inoculate 50 mL fresh YNBUP medium containing 8.4% xylose or 9.4% glucose in a 125-mL Erlenmeyer flask. The starting cell density was approximately 0.9 g L$^{-1}$. The cultures were then grown at 20° C. with shaking at 100 rpm. Samples were drawn daily and analyzed by HPLC as described above.

Q. Respiration measurement

P. stipitis strains were grown overnight in YNBUP-xylose (2%) medium under aerobic conditions. Then half of the overnight-grown cells were transferred to 25 mL fresh medium to grow for 16 h to mid-log phase under the same conditions. The cells were harvested and washed in an assay buffer containing 20 mM potassium phosphate (pH7.0) and 5 mM magnesium chloride. The cells were resuspended in 500 μL of the same buffer for assays. Oxygen uptake was measured by using a Clark type of electrode (Yellow Spring Instrument). The assay was performed in an assay buffer containing 20 mM potassium phosphate, 5 mM magnesium chloride, plus xylose or glucose (2%) as the substrate at 30° C. The assay buffer was saturated with air before the experiment. Ten to fifty μL of cells were injected into the assay chamber and the total reaction volume was 2 mL. Antimycin A, SHAM or rotenone was dissolved in dimethyl formamide while potassium cyanide was dissolved in water. Inhibitor solution was injected into the chamber after adding the cells.

R. Oxygen utilization kinetic studies

P. stipitis strains were grown under aerobic conditions in 25 mL of YNBUP medium in a 125-mL baffled flask containing 2% xylose. The cells were shaken at 140 rpm at 30° C. for overnight. No ethanol was formed under this growth condition. Half of the overnight cultures were then used to inoculate 25 mL of the same medium and the cells were cultivated under the same conditions for 12 h. The cells were harvested and washed twice with 20 mM potassium phosphate buffer (pH 7.0) plus 5 mM magnesium chloride, and resuspended in 1.2 mL of the same buffer. Half of the cells were used for dry weight determination while the other half was used for oxygen uptake measurements. Oxygen consumption curves were obtained by injecting cells in an assay buffer containing 20 mM potassium phosphate, 5 mM magnesium chloride, plus 2% xylose as the substrate at 30° C. The oxygraphic curve was recorded from 100% to 0% of air. Thirty to sixty μL of cells were used in the measurements. The assay buffer was saturated with air before the experiment. The dissolved oxygen concentration at 30° C. is 237 μM. The data were plotted using the Origin program (Microcal Software).

II. Results

A. Cloning of the PsSTO1 gene

To clone PsSTO1 from P. stipitis, we aligned the available fingal Sto protein sequences, and found that they are highly conserved in two regions IFLES(I/V)AGVPGMV and HRFVGYLEEEAV. The first region contains a putative ubiquinol binding site (Berthold, 1998; Andersson and Nordlund, 1999) while the second region contains a highly conserved ion-binding motif (Vanlerberghe and McIntosh, 1997). Even though these two segments are highly conserved, the organisms and their codon usage may have diverged significantly. We first developed a codon usage table for *P. stipitis* using 19 cloned genes (obtained by using database: http://www.dna.affrc.go.jp/~nkamura/). We then amplified a 293-bp region, which is located in the center of PsSTO1 from wild-type genomic DNA of CBS 6054. This segment displayed 70% similarity at the DNA level with the STO genes from two other yeast species, *Pichia anomala* and *Candida albicans*. It was then used as the starting point for genome walking to clone the entire PsST01 gene.

For the walking strategy, five linear fragment libraries were constructed as described in Methods. For the 5' end walking, two overlapping PsSTO1 fragments (1.7 kb and 4 kb) were obtained from the PvuII and the StuI libraries. For the 3' end walking, five different lengths of overlapping PsSTO1 fragments were obtained from the five libraries. Sequencing of all the fragments allowed the merging of the coding region of 1071 bp, and about 1.0 kb each for the 5' and 3' flanking regions.

B. The biochemical properties of the PsSto protein

The open reading frame of PsSTO1 encodes for 357 amino acids. The deduced molecular weight for the predicted protein is about 41,326 daltons. It has a calculated pI of 9.1. These values are comparable to values reported for Sto proteins from other yeast and fungi (Huk and Kang, 1999; Sajoko et al., 1993). A hydrophobicity plot of the PsSto protein revealed two trans-membrane helices that are similar to all reported Sto proteins. A deduced cleavage site for the signal peptide is predicted at the $27^{th}$ amino acid after the methione start codon.

C. Putative 5' cis-acting elements

A search in the 5' untranslated region (UTR) for cis-acting elements revealed two putative TATA boxes at −86 to 79, −194 to −187. Other putative binding sites included a 25-bp AT segment of mitochondrial control region (−158 to −133), a common transcriptional activator responding to stress signals, AP-1 (−689 to−683), an Adh-UAS2 sequence (−666 to −659), a heat shock factor (hsp70) and a nitrogen-regulatory element (−756 to −743). These observations indicated that the PsSTO1 gene could be regulated by various environmental signals.

D. PsSTO1 does not contain introns

Because introns are found in several fungal STO genes, we decided to examine whether PsSTO1 contains introns. RT-PCR was performed on wild-type CBS 6054 cells grown on YNB-xylose under fully aerobic conditions. A single 1.1-kb band of RT-PCR product, which was similar in size to the genomic PCR product of PsSTO1, was observed. Complete sequencing of the cloned RT-PCR products revealed that there was no intron present in the PsSTO1 gene.

E. Phylogenetic studies of the fungal Sto proteins

A phylogenetic tree drawn using eight Sto proteins from yeast and filamentous fungi showed that they broke into two separate branches (FIG. 1). PsSto showed 53% identity to these yeast and fungal counterparts. However, PsSTO1 displayed 33% identity to three other yeast STO genes at the DNA level, and 64% identity at the amino acid level. The PsSto is most closely related to the Sto of *P. anomala*.

F. Construction of a sto1-Δmutant in *P. stipitis*

Figure 2:
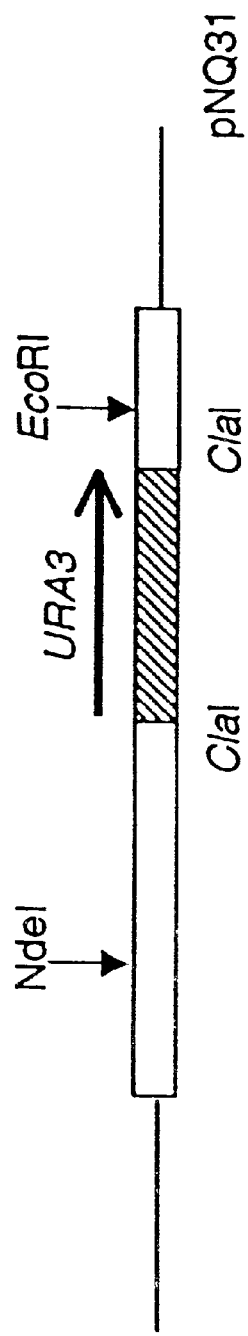
FIG. 2 is a schematic representation of the PsSto disruption cassette; open box represents PsSto sequence and hatched box represents the PsURA3 gene.

Disrupting the STO1 gene in *P. stipitis* had two purposes. First, we needed to ensure that the cloned sequence encodes for Sto. Second, we hoped to obtain a mutant with the STO pathway impaired, so the electrons only go through the cytochrome c oxidase. This mutant would be used to compare with the cytochrome c disruptant obtained earlier to elucidate the physiological roles of alternative respiration in *P. stipitis*. To do that, a one-step gene replacement was employed by inserting the PsURA3 gene in the middle of the PsSTO1 coding region in FPL-UC7 (FIG. 2). The putative disruptants of sto1-Δ were screened by colony PCR. They all showed a single 2.4-kb band, which corresponded to the size of the coding region of PsSTO1 plus the inserted PsURA3 gene. The parental strain, FPL-UC7, only showed a 1.1-kb coding region band.

A double mutant (cycl-Δ, sto1-Δ) was attempted in a *P. stipitis* host strain, FPL-PLU5 (Lu et al., 1998) which has two selectable markers. However, the putative double knockout colonies were small as pinpoints. They were not viable after being transferred onto selective medium without uridine and leucine. We therefore concluded that at least one of the respiratory pathways must be present to support cell growth under the conditions we used for cell cultivation.

G. Respiratory inhibitor studies

One sto1Δ strain, was named FPL-Shi31, and it was confirmed by measuring respiration in the presence of inhibitor antimycin A or SHAM. SHAM blocks Sto probably by interfering with the ubiquinol binding site (Berthold, 1998). Upon adding 4 mM SHAM to the sto1Δ cells pre-grown on YNB-xylose (2%), the respiration trace did not show any change. This suggested that the SHAM-sensitive respiration in this mutant was totally impaired due to the loss of the structural gene. On the other hand, when 10 $\mu$M antimycin A, an inhibitor that blocks electron transfer from the cytochrome bc1 complex to cytochrome c, was added to the cells of the sto1Δ mutant, respiration dropped to zero. This observation indicated that the mutant was unable to sustain any respiration when the CYT pathway was blocked. Conversely, FPL-Shi21 (cyc1Δ) displayed insensitivity to antimycin A and respiration was completely blocked by SHAM.

H. No other Sto isoforms were induced in the sto1Δ strain

To determine whether there were any isoforms of Sto present in the sto1Δ mutant (FPL-Shi31), we isolated mitochondrial proteins from four strains of *P. stipitis*. A monoclonal antibody raised against Sto from *Savromatum guttatum* (voodo lily) was used to cross-react with the PsSto. In the samples from CBS 6054, FPL-UC7 and FPL-Shi21, only a single 39 kd band was observed, which corresponded to the size of mature Sto proteins from other yeasts. However, this band was missing from the FPL-Shi31 sample in which the PsSTO1 was disrupted. This result indicated that no isoforms of Sto are induced in FPL-Shi31. Thus, the Sto in *P. stipitis* FPL-UC7 is encoded by a single gene, which is similar to the cases reported in *P. anomala* (Sakajo et al., 1993) and the rice-blast fungus, *Magnaporthe grisea* (Yukioka et al., 1998). These results also confirmed that we had obtained a mutant in which the STO respiration was totally blocked. Therefore, cytochrome c oxidase is the only functional terminal oxidase in the sto1Δ mutant.

I. Cytochrome spectra study in the sto1Δ strain

Because the components of the STO pathway in *P. stipitis* were unclear, we decided to examine the cytochrome contents in the sto1Δ mutant to see if any changes occurred in the sto1Δ mutant. Cells of the sto1Δ mutant and the parental strain were cultivated in three media. In the initial studies, the cytochome b, c, cl, and a·$a_3$ from the mutant appeared to be at normal levels under spectro-microscopic examinations. Subsequent low temperature recordings of both the mutant and parent cells grown on xylose medium was also performed. Cytochromes b, c, and c1 from the mutant showed no significant differences from those observed in the parental strain. This indicated that deletion of PsSTO1 in *P. stipitis* does not alter the levels of cytochromes b, c, and c1 in the cell. The a·a$_3$ peak in the mutant was slightly higher than the parent. The small increase in a·a$_3$ suggested that the deletion of Sto might affect the level of the remaining cytochrome c oxidase (a·a$_3$). We therefore concluded that the STO pathway does not contain cytochromes as functional components.

J. Introducing PsSTO1 in *S. cerevisiae* strains

We expressed PsSTO1 in *S. cerevisiae* for two purposes. First, we wanted to determine whether PsSto could confer cyanide-resistant respiration in a Crabtree-positive yeast, *S. cerevisiae*, which does not have the STO pathway. Second, we wanted to examine how PsSto functioned in a Crabtree-positive physiological background. The PsSTO1 gene was introduced into two different *S. cerevisiae* strains, 679a and B06748. 679α is a strain that has normal respiration capacity (Culbertson, personal communication). By expressing PsSTO1 in this strain, we could evaluate the effect on its respiration capacity after getting an additional terminal oxidase. Both oxidases would accept electrons from the rotenone-insensitive NADH dehydrogenases. On the other hand, B06748 is a cytochrome c null mutant (Holzschu et al., 1987) due to the deletion of the ScCYC1 and ScCYC7, which encode the two isoforms of the cytochrome c. As previously reported, deleting cytochrome c in *S. cerevisiae* and other yeasts can lead to simultaneous disappearance of cytochrome a·a$_3$ (Cox) (Bottorff et al., 1991; Pearce, 1995; Shi et al., 1999). Therefore, it is unable to accept electrons from the cytochrome respiratory chain. Therefore, B06748 is a slow grower and uses fermentation to generate energy. In this genetic background, we could evaluate the effect of using Sto as the only terminal oxidase in a Crabtree-positive yeast. A constitutive ScGAPDH promoter was used to drive the PsSTO1 gene in both strains (FIG. 3.11A).

Genomic PCR was used to confirm that the transformants bear either the pNQ32 plasmid or the empty vector, pYPR2831, in 679α or B06748 (data not shown). For the 679α transformants, we measured oxygen consumption rates from the cells grown aerobically in the presence of glucose. Oxygen uptake experiments showed that the respiration rate from 679α (pNQ32) is 63% higher than that recorded from the control. This indicated that introduced Sto contributed to the increased respiratory capacity in transformed strain. Our observations resembled the reports on the functional expression of Sto of *Candida albicans* in *S. cerevisiae* (Huh and Kang, 1999) and Sto of *S. guttatum* in *Schizosaccharomyces pombe* (1996). Because the Sto is resistant to cyanide, an inhibitor that blocks the activity of the cytochrome c oxidase, we also measured the respiration rate in the presence of 1 mM KCN. Upon adding KCN to the cells, the 679α (pNQ32) strain containing PsSTO1 was able to show about 4-fold higher cyanide-resistant respiration than the control. We observed a similar result when 10 μM antimycin A was used as the inhibitor (data not shown).

Figure 3A:
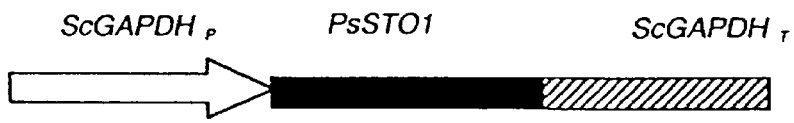
FIG. 3A shows the construction of a PsSTO1 expression cassette having a *Saccharomyces cerevisiae* promoter and terminator sequence.
Figure 3B:
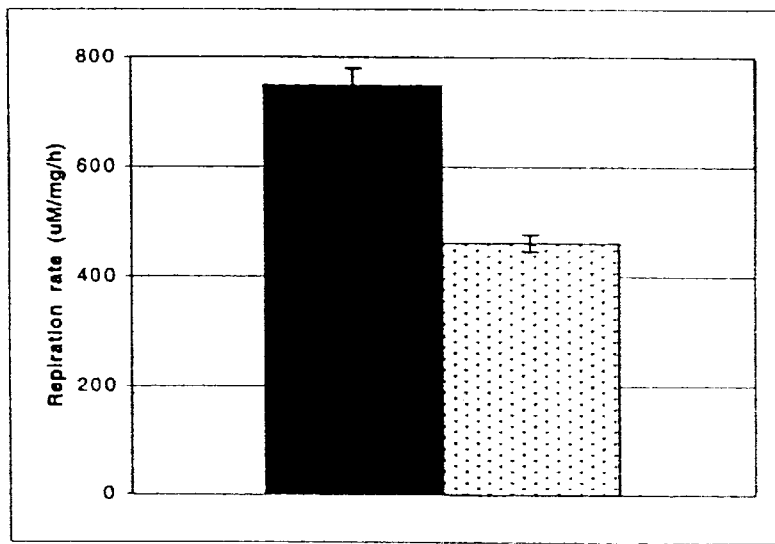
FIGS. 3B and 3C compare the respiration rate of *S. cerevisiae* expressing PsSTO1 (solid) and *S. cerevisiae* lacking PsSTO1 (hatched) without inhibitor (FIG. 3B) and in the presence of 1 mM KCN (FIG. 3C).
Figure 3C:
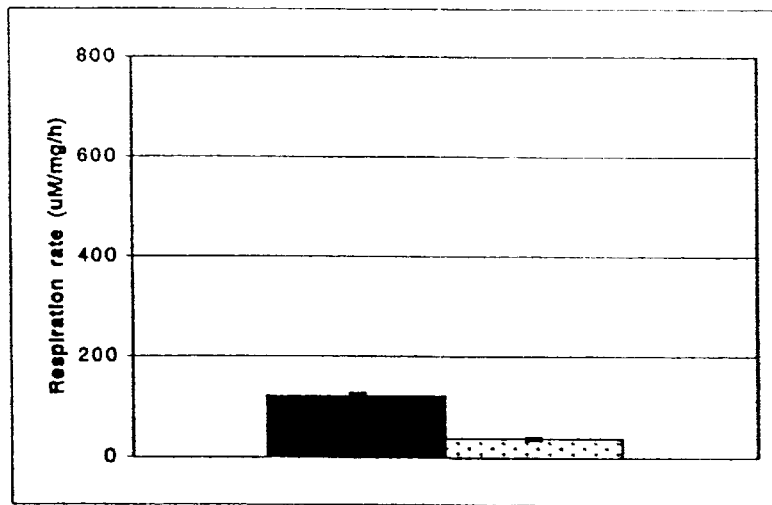

For the B06748 transformants, a respiro-fermentation trial was conducted under oxygen-limited conditions instead of the respiration consumption measurements. The growth condition used was to induce the respiration from the introduced PsSto. In the trial, the transformed strain containing PsSTO1 showed no significant difference in cell growth from the control strain (FIG. 3A). This indicated that Sto is not phosphorylating. However, the transformed strain bearing PsSTO1 showed a slower glucose utilization rate (FIG. 3B) and a lower ethanol production rate (FIG. 3C) than the control strain. These observations suggested that the introduced PsSto could support electron transport as a terminal oxidase in the B06748 background. Taken all the data in this section together, we concluded that introducing PsSTO1 in *S. cerevisiae* could impart a functional cyanide-resistant pathway.

K. Aerobic growth results

The sto1-Δ mutant (FPL-Shi31) was then tested for its growth capacities on non-fermentative carbon sources. The parental strain, FPL-UC7 and the cyc1-Δ mutant (FPL-Shi21) were used as the controls. The sto1Δ mutant showed no significant difference from the parent when it was cultivated on glycerol as a carbon source. However, it showed higher cell density in the ethanol medium than the parent indicating that this strain could oxidize ethanol more quickly than the parental strain. Conversely, the cyc1Δ mutant (FPL-Shi21) showed no growth during the 16 h experiment on glycerol and ethanol, which matched the previous observations (Shi et al., 1999).

L. Shake-flask respiro-fermentation results

Figure 4A:
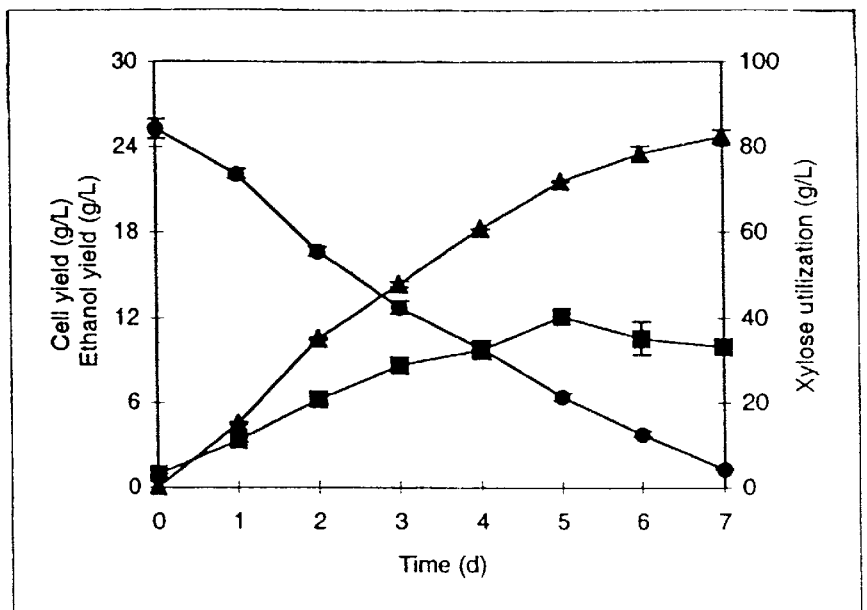
FIG. 4 compares the cell growth (■), ethanol production (▲), and xylose utilization (●) of PsSto disruptant FPL-Shi31 (FIG. 4A) and the cell growth (□), ethanol production (△), and xylose utilization (○) of FPL-UC7.
Figure 4B:
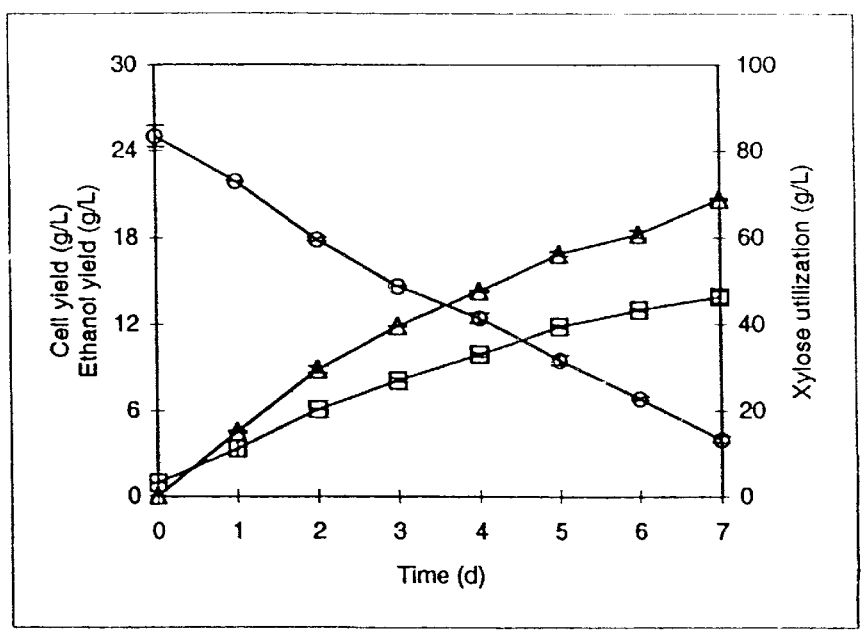

To evaluate the effects of losing the STO pathway to the respiro-fermentative capacity of the mutant, the sto1Δ strain was tested for its growth and ethanol production rates in medium containing 8.4% xylose or 9.4% glucose. In xylose medium, the growth of mutant showed no significant difference from the parent in the first five days. The mutant stopped growing after day 5 while the parent continued to grown until the end of the trial. However, the volumetric ethanol production rate from the sto1Δ strain on xylose was approximately 20% higher than that from the parent. The mutant also appeared to use xylose faster than the parent (FIGS. 4A and 4B). The mutant did not accumulate any significant amounts of polyols. Interestingly, the mutant did not exhibit significant differences in cell yield, ethanol production rate or sugar utilization rate from the parental strain when grown on glucose. In a separate trial to test the ethanol re-oxidation rate of the sto1Δ strain and the cyc1Δ strain, cells from the two strains were grown in YP medium containing 2% xylose. Both strains consumed all the sugars in 36 h. They then began to use the ethanol to support growth. The ethanol re-assimilation rate for the sto1Δ strain was faster than the cyc1Δ strain and the parent.

M. Respiration rate of sto1Δ strain

To test whether the deletion of Sto in sto1Δ strain would affect its respiratory capacity, oxygen consumption rates of the mutant grown in xylose and glucose media were measured. Respiration rates from the parental and the cyc1Δ strains were also measured for comparison. For xylose-grown cells, respiration rate was measured using 2% xylose as the assay substrate. The xylose-grown cells of the sto1Δ mutant showed approximately 21% higher respiration rate than the parent. However, the cyc1Δ mutant showed twofold higher respiration rate than the parent. For glucose-grown cells, respiration rate was measured using 2% glucose as the assay substrate. The glucose-grown cells of the sto1Δ mutant did not show significant difference in the oxygen consumption rate to the parent. The cyc1Δ mutant displayed threefold higher respiration rate than the parent. These results suggested that losing one respiratory pathway could affect the activity of the other system. This effect is more dramatic in the cyc1Δ mutant, which loses the major energy-generating CYT pathway.

N. Measurement of the oxygen utilization kinetics

Due to our primary interest in understanding the oxygen requirement for xylose utilization in *P. stipitis*, we compared the oxygen affinity constants of the Sto and Cox. In this study, we created two *P. stipitis* mutants, cyc1Δ (FPL-Shi21) and sto1Δ (FPL-Shi31), each of which has a single functional terminal oxidase. These mutants were obtained from the same genetic background, so other factors were similar. Oxygen affinity of Sto and Cox were studied using xylose as the substrate.

In physiological studies, the $K_m$ (O2) values can be calculated from the non-linear region of an oxygraphic curve. This occurs between the linear region, in which oxygen saturates the uptake system, and 0% oxygen where oxygen consumption stops. This can be measured at whole cell level (Rice and Hempfling, 1978; Dubreucq et al., 1990). In this non-linear region, oxygen uptake rates (V) at different oxygen concentrations (S) can be deduced. By using V as a function of the oxygen concentration at which the tangent is drawn, the $K_m$ value can be deduced from a double-reciprocal plot of oxygen uptake rates against oxygen concentrations. $V_{max}$ measured, in this case, is the oxygen consumption rate of each pathway, which corresponds to its theoretical maximum capacity. The deduced $1/K_m$ value reflects the affinity of the oxidase to oxygen. In this experiment, the affinity constant represents the affinity of the oxidase as the electron donor with regard to oxygen, which is used as the electron acceptor.

Xylose-grown cells of FPL-Shi21 and FPL-Shi31 were used in this study. The educed $K_m$ and $V_{max}$ values were obtained. Under our growth condition, the deduced $K_m$ of Cox was 1.6-fold higher than that of Sto indicating Sto has higher affinity to oxygen than Cox. The $K_m$ of PsSto is in line with those reported before from plant mitochondria (0.5–2 $\mu$M, Ribas-Carbo et al., 1994

O. *P. stipitis* employs different proton-translocating sites during xylose or glucose metabolism Because certain Crabtree-negative yeasts contain different NADH oxidation systems, we decided to test if the rotenone-sensitive or the rotenone-insensitive NADH dehydrogenases are present in *P. stipitis*. This study is very important because it will provide information on the first component of the respiratory systems in *P. stipitis*. This information can also aid in understanding the functional organization of the STO pathway. The NADH dehydrogenase complex I (Complex I or Site I) is sensitive to rotenone while the internal and external NADH dehydrogenases are resistant to it. The internal or the external NADH dehydrogenase can be distinguished by their different temperature dependency (Marx and Brinkman, 1978).

In the first trial, we measured respiration from aerobically xylose- or glucose-grown cells of wild-type CBS 6054 *P.stipitis* in the presence of rotenone. When 0.1 mM rotenone was injected to the glucose-grown cells of CBS 6054, the cells died and floated in the chamber within 1 minute of injection. This indicated that these cells were sensitive to rotenone and could not sustain any respiration. Conversely, when 0.1 mM rotenone was injected to the xylose-grown cells of CBS 6054, respiration was sustained and the rate was similar to that detected from the untreated cells (Table 4). Rotenone-insensitive NADH dehydrogenases are present in the xylose-grown cells, which enables the cells to by-pass Site I. A subsequent trial was performed on the xylose- and glucose-grown cells in four *P. stipitis* strains. Xylose-grown cells of wild type CBS 6054 and the parental strain, FPL-UC7, displayed insensitivity to rotenone. However, the xylose-grown cells of the sto1$\Delta$ and the cyc1$\Delta$ mutants were rotenone-sensitive. On the other hand, the glucose-grown cells of the four strains were rotenone-sensitive (Table 5). These results implied that there might be a fundamental difference in numbers of proton-translocating sites present in cells during xylose and glucose metabolism.

The present invention is not limited to the exemplified embodiments, but is intended to encompass all such modifications and variations as come within the scope of the following claims.

TABLE 4

Oxygen consumption rates of cells of *P. stipitis* wild-type CBS 6054 in the presence or absence of 0.1 mM rotenone.

| Glucose-grown cells | | Xylose-grown cells | |
|---|---|---|---|
| | $\mu$M · mg$^{-1}$ · h$^{-1}$ | | |
| −rotenone | +rotenone | −rotenone | +rotenone |
| 2.9 ± 0.1 | ND$^a$ | 4.5 ± 0.2 | 4.6 ± 0.2 |

TABLE 5

Rotenone sensitivity experiment on four *P. stipitis* strains in the presence of 0.1 mM rotenone

| | Strains | | | |
|---|---|---|---|---|
| | Wild-type CBS6054 | FPL-UC7 (ura3-3) | FPL-Shi31 (sto1–$\Delta$) | FPL-Shi21 (cyc1–$\Delta$) |
| Xylose-grown cells | + | + | − | − |
| Glucose-grown cells | − | − | − | − |

+: Cells sustained rotenone-insensitive respiration
−: Cells could not sustain rotenone-insensitive respiration

REFERENCES

Andersson, M. E. and P. Nordlund. (1999) A revised model of the active site of alternative oxdiase. FEBS Lett. 449:17–22.

Bonner, W. D. Jr., S. D. Clark, and P. R. Rich. (1986) Partial purification and characterization of the quinol oxidase activity of *Arum maculatum* mitochondria. Plant Physiol. 80:838–842.

Bottorff, D. A., S. Parmaksizoglu, E. G. Lemire, J. W. Coffin, H. Bertans, and F. E. Nargang. (1994) Mutations in the structural gene for cytochrome c result in deficiency of both cytochromes a.a3 and c in *Neurospora crassa*. Curr. Genet. 26:329–335.

Calhoun, M. W., K. L. Oden, R. B. Gennis, M. J. T. de Mattos, O. M. Neijssel. (1993) Energetic efficiency of *Escherichia coli*: effects of mutations in components of the aerobic respiratory chain. J. Bacteriol. 175:3020–3025.

Cho, J. Y. and T. W. Jeffries. (1999) Transcriptional control of ADH genes in the xylose-fermenting yeast *Pichia stipitis*. Appl. Environ. Microbiol. 65:2363–2368.

Ciriacy, M. (1975) Genetics of alcohol dehydrogenase in *Saccharomyces cerevisiae*. II. Two loci controlling synthesis of the glucose-repressible ADH II. Mol. Gen. Genet. 138:157–64.

Crabtree, H. G. (1929) Observations of the carbohydrate metabolism in tumors. Biochem. J. 23:536–545.

Dawson, A. G. (1979) Oxidation of cytosolic NADH formed during aerobic metabolism in mammalain cells. Trends Biochem. Sci. 4:171–176.

Defontaine, A., F. M. Lecocq, and J. N. Hallet. (1990) A rapid miniprep method for the preparation of yeast mitochondrial DNA. Nucleic Acids Res. 19:185–190.

De Vries, S. and C. A. M. Marres. (1987) The mitochondrial respiratory chain of yeast. Structure and biosynthesis and the role in cellular metabolism. Biochim. Biophys. Acta 895:205–239. De Vries, S. and L. A. Grivell. (1988) Purification and characterization of a rotenone-insensitive NADH:Q6 oxidoreductase from mitochondria of *Saccharomyces cerevisiae*. Eur. J. Biochem. 176:377–384.

De Winde, J. H. and L. A. Grivell. (1993) Global regulation of mitochondrial biogenesis in *Saccharomyce cerevisiae*. Prog. Nucleic Acid Res. Mol. Biol. 46:51–91.

Douce, R. and M. Neuburger. (1989) The uniqueness of plant mitochondria. Annu. Rev. Plant Physiol. Plant Mol. Biol. 40:371–414.

Dubreucq, E., H. Boze, G. Moulin, and P. Galzy. (1990) Alternative respiration pathways in *Schwanniomyces castellii* II. Characteristics of oxidation pathways. Ant. van Leeuwenhoek 57:131–137.

Elthon, E. T., R. L. Nickels, and L. McIntosh. (1989) Monoclonal antibodies to the alternative oxidase of higher plant mitochondria. Plant Physiol. 89:1311–1317.

Gennis, R. B. and V. Stewart. (1996) In *Escherichia coli* and Salmonella: cellular and molecular biology. Neidhardt, F. C. (eds). Washington, D. C., ASM Press. pp. 217–261.

Guvinden, R. (1995) Molecular and biochemical characterization of ethanolic D-xylose fermenting *Pichia stipitis, Candida shehatae* and their fusants. Master Thesis, University of Durban-Westville, Durban, South Africa.

Hickey, D. R., K. Jayaraman, C. T. Goodhue, J. Shah, S. A. Fingar, J. M. Clements, Y. Hosokawa, S. Tsunasawa, and F. Sherman. (1991) Synthesis and expression of genes encoding tuna, pigeon, and horse cytochrome c in the yeast *Saccharomyces cerevisiae*. Gene 105:73–81.

Hoefnagel, M. H. N., H. A. Millar, J. T. Wiskich, and D. A. Day. (1995) Cytochrome and alternative respiratory pathways compete for electrons in the presence of pyruvate in soybean mitochondria. Arch. Biochem. Biophys. 318:394–400.

Holzschu, D., L. Principio, K. T. Conklin, D. R. Hickey, J. Short, R. Rao, G. McLendon, and F. Sherman. (1987). Replacement of the invariant lysine 77 by arginine in yeast iso-1-cytochrome c results in enhanced and normal activities in vitro and in vivo. J. Biol. Chem. 262:7125–7131.

Horiuchi H, T. Ashikari, T. Amachi, H. Yoshizumi, M. Takagi, and K. Yano. (1990) High-level secretion of a *Rhizopus niveus* aspartic proteinase in *Saccharomyces cerevisiae*. Agric. Biol. Chem. 54:1771–1779.

Huh, W.-K. and S.-O. Kang. (1999) Molecular cloning and functional expression of alternative oxidase from *Candida albicans*. J. Bacteriol. 181:4098–4102.

Jeppsson, H., N. J. Alexander, and B. Hahn-HNgerdal. (1995) Existence of cyanide insensitive respiration in the yeast *Pichia stipitis* and its possible influence on product formation during xylose utilization. Appl. Environ. Microbiol. 61:2596–2600. Keilin, D. (1929) Cytochromes and respiratory enzymes. Pro. R. Soc. B 104:206–252.

Kimura, M. (1983) The neutral theory of molecular evolution. Cambridge University Press, Cambridge, UK.

Larsson, C., I.-L. Pahlman, R. Ansell, M. Rigoulet, L. Adler, and L. Gustafsson. (1998) The importance of the glycerol 3-phosphate shuttle during aerobic growth of *Saccharomyces cerevisiae*. Yeast 14:347–357.

Lehninger, A. L. (1955) In The Harvey Lectures 1953–1954. New York, Academic Press, pp, 176–215.

Ligthelm, M. E. (1987) The role of oxygen in the fermentation of D-xylose to ethanol by yeasts. Ph.D. Thesis. University of The Orange Free State, Bloemfontein, South Africa.

Lloyd, D. and S. W. Edwards. (1977) Electron transport pathways: alternative to the main phosphorylating respiratory chain, in: 11th FEBS meeting Copenhagen, Functions of alternative terminal oxidases. 49:1–10.

Lu, P., B. P. Davis, J. Hendrick, and T. W. Jeffries. (1998) Cloning and disruption of the β-Isopropylmalate dehydrogenase gene (LEU2) of *Pichia stipitis* with URA3 and recovery of the double auxotroph. Appl. Microbiol. Biotechnol. 49:141–146.

Luttik, M. A., K. M. Overkamp, P. Kitter, S. de Vries, J. P. van Dijken, and J. T. Pronk. (1998) The *Saccharomyces cerevisiae* NDE1 and NDE2 genes encode separate mitochondrial NADH dehydrogenases catalyzing the oxidation of cytosolic NADH. J. Biol. Chem. 273:24529–24534.

Marres C. A. M., S. de Vries, and L. A. Grivell. (1991) Isolation and inactivation of the nuclear gene encoding the rotenone-insensitive internal NADH:ubiquinone oxidoreductase of mitochondria from *Saccharomyces cerevisiae*. Eur. J. Biochem. 195:857–862.

Medentsev, A. G. and V. K. Akimenko. (1999) Development and activation of cyanide-resistant respiration in the yeast *Yarrowia lipolytic*. Biochem. (Moscow) 64:945–951.

Meyrial, V., J. P. Delegenes, C. Romieu, R. Moletta, and A. M. Gounot. (1995). Ethanol tolerance and activity of plasma-membrane ATPase in *Pichia stipitis* grown on D-xylose or on D-glucose. Enzyme Microb. Technol. 17:535–540.

Minagawa, N., S. Sakajo, T. Komiyama, and A. Yoshimoto. (1990) Essential role of ferrous iron in cyanise-resistant respiration in *Hansenula anomala*. FEBS Lett. 267:114–116.

Moller, I. M., and W. Lin. (1986) Membrane-bound NAD(P)H dehydrogenases in higher plant cells. Annu. Rev. Plant Physiol. 37:309–334.

Moore, A. L. and P. R. Rich. (1985) Organization of the respiratory chain and oxidative phosphorylation. Douce, R., Mannella, C., Bonner, W. D (eds). Encyclopedia of Plant Physiology 18:134–172.

Moore, A. L., A. L. Umbach, and J. N. Siedow. (1995a). The active site of the cyanide-resistant oxidase from plant mitochondrial contains a binuclear ion center. FEBS Lett. 362:10–14.

Moore, A. L., A. L. Umbach, and J. N. Siedow. (1995b). Structure-function relationships of the alternative oxiase of plant mitochondria: a model of the active site. J. Bioenerg. Biomembr. 27:367–377.

Ohnishi, T. (1972) Factors controlling the occurrence of site I phosphorylation in *Candida utilis* mitochondria. FEBS Lett. 24:305–309.

Ohnishi, T. (1973) Mechanism of electron transport and energy conservation in the site I region of the respiratory chain. Biochim. Biophys. Acta 301:105–128.

Passoth, V., M. Zimmermann, and U. Klinner. (1996) Peculiarities of the regulation of fermentation and respiration in the Crabtree-negative, xylose-fermenting yeast *Pichia stipitis*. Appl. Biochem. Biotech. 57/58:201–212.

Passoth, V., B. Schafer, B. Liebel, T. Weierstall, and U. Klinner. (1998) Molecular cloning of alcohol dehydrogenase genes of the yeast *Pichia stipitis* and identification of the fermentative ADH. Yeast 14:1311–1325.

Pearce, D. A., and F. Sherman. (1995) Degradation of cytochrome oxidase sub units in mutants of yeast lacking cytochome c, and suppression of the degradation by mutation of yme1. J. Biol. Chem. 270:20879–20882.

Poinsot, C., G. Moulin, M. L. Claisse, and P. Galzy. (1986) Isolation and characterization of a mutant of *Schwanniomyces castellii* with altered respiration. Ant. van Leeuwenhoek 53:65–70.

Querol, A. and E. Barrio. (1991) A rapid and simple method for the preparation of yeast mitochondrial DNA. Nucleic Acids Res. 18:1657–1660.

Ribas-Carbo, M., J. A. Berry, J. Azcon-Bieto, and J. N. Siedow. (1994) The reaction of the plant mitochondrial cyanide-resistant alternative oxidase with oxygen. Biochim. Biophys. Acta 1188:205–212.

Rice, C. W. and W. P. Hempfling. (1978) Oxygen-limited continuous culture and respiratory energy conservation in *Escherichia coli*. J. Bacteriol. 134:115–124.

Sakajo, S., N. Minagawa, and A. Yoshimoto. (1993) Characterization of the alternative oxidase protein in the yeast Hansenula anomala. FEBS Lett. 318:310–312.

Sánchez, O., R. E. Navarro, and J. Aguirre. (1998) Increased transformation frequency and tagging of developmental gene in *Aspergillus nidulans* by restriction enzyme-mediated integration (REMI). Appl. Microbiol. Biotechnol. 258:89–94.

Saraste, M. (1999) Oxidative phosphorylation at the fin de siäcle. Science 283:1488–1490.

Seidow, J. N. (1982) The nature of cyanide-resistant pathway in plant mitochondria. Rec. Adv. Phytochem. 16:47–84.

Sherman, F., J. W. Stewart, M. Jackson, R. A. Gilmore, and J. H. Parker. (1974) Mutants of yeast defective in iso-1-cytochrome c. Genetics 77:255–284.

Shi, N. Q., B. P. Davis, F. Sherman, J. Cruz, and T. W. Jeffries. (1999) Disruption of a cytochrome c gene in xylose-utilizing yeast *Pichia stipitis* leads to higher ethanol production. Yeast 15:1021–1030.

Shi, N. Q. and T. W. Jeffries. (1998) Anaerobic growth and improved fermentation of *Pichia stipitis* bearing a URA1 gene from *Saccharomyces cerevisiae*. Appl. Microbiol. Biotechnol. 50:339–345.

Skoog, K. and B. Hahn-Hägerdal. (1990) Effect of oxygenation on xylose fermentation by *Pichia stipitis*. Appl. Environ. Microbiol. 56:3389–3394.

Slininger, P. J., L. E. Branstrator, R. J. Bothast, M. R. Okos, and M. R. Ladisch. (1991) Growth, death, and oxygen uptake kinetics of *Pichia stipitis* on xylose. Biotechnol. Bioeng. 37:973–980.

Small, W. C. and L. McAlister-Henn. (1998) Identification of a cytosolically directed NADH dehydrogenase in mitochondria of *Saccharomyces cerevisiae*. J. Bacteriol. 180:4051–4055.

Storey, B. T. (1976) Respiratory chain of plant mitochondria. XVIII. Point of interaction of the alternate oxidase with respiratory chain. Plant Physiol. 58:521–525.

Van Dijken, J. P. and W. A. Scheffers. (1986) Redox balances in the metabolism of sugars by yeasts. FEMS Microbiol. Rev. 32:199–224.

Vanlerberghe G. C. and L. McIntosh. (1997) Alternative oxidase: from gene to function. Annu. Rev. Plant Physiol. Plant Mol. Biol. 48:703–734.

Weidner, U., S. Geier, A. Ptock, T. Friedrich, H. Leif, and H. Weiss.(1993) The gene locus of the proton-translocating NADH:ubiquinone oxidoreductase in *Escherichia coli*: Organization of the 14 genes and relationship between the derived proteins and sub units of mitochondrial complex I. J. Mol. Biol. 223:109–122.

Wilson, S. B. (1980) Energy conservation by the plant mitochondrial cyanide-insensitive oxidase. Biochem. J. 190:349–360.

Yukioka, H., S. Inagaki, R. Tanaka, K. Katoh, N. Miki, A. Mizutani, and M. Masuko. (1998) Transcriptional activation of the alternative oxidase gene of the fungi *Magnaporthe grisea* by a respiratory-inhibiting fungicide and hydrogen peroxide. Biochim. Biophys. Acta 1442:161–169.

Zimmer, E., B. Blanchard, H. Boze, G. Moulin, and P. Galzy. (1997) Glucose metabolism in the yeast *Schwanniomyces castellii*: Role of phosphorylation site I and an alternative respiratory pathway. Appl. Environ. Microbiol. 63:2779–2784.

We claim:

1. An isolated polynucleotide comprising a sequence encoding the *Pichia stipitis* SHAM-sensitive terminal oxidase of SEQ ID NO:26.

2. The polynucleotide of claim 1, wherein the sequence comprises SEQ ID NO:25.

3. A vector comprising the sequence of claim 1.

4. An isolated xylose-fermenting mutant of a yeast or fungal species, the mutant having reduced SHAM-sensitive terminal oxidase relative to the level of SHAM-sensitive terminal oxidase in the parent strain from which the mutant was derived, the parent strain comprising a SHAM-sensitive terminal oxidase coding sequence, the coding sequence being amplifiable by polymerase chain reaction using a suitable primer pair, each primer comprising a polynucleotide sequence the trabslation product of which comprises SEQ ID NO:26.

5. The mutant of claim 4, wherein the mutant ferments xylose at an increased rate relative to the parent strain from which the mutant was derived.

6. The mutant of claim 4, wherein the mutant is a SHAM-sensitive terminal oxidase disruptant mutant.

7. The mutant of claim 4, wherein reduced expression of SHAM-sensitive terminal oxidase is effected by expressing in the mutant an antisense RNA complementary to SHAM-sensitive terminal oxidase mRNA.

8. The mutant of claim 4, wherein the species is selected from the group consisting of *Pichia stipitis*, Group I species, and Group II species, wherein Group I species natively comprise a cytochrome pathway and a SHAM-sensitive pathway, and wherein Group II species natively comprise a cytochrome pathway, an antimycin A- and SHAM-insensitive pathway, and a SHAM-sensitive pathway.

9. An isolated xylose-fermenting mutant of *Pichia stipitis*, the mutant having reduced having reduced SHAM-sensitive terminal oxidase relative to the level of SHAM-sensitive terminal oxidase in the parent strain from which the mutant was derived.

10. The mutant of claim 9, wherein the parent strain is selected from the group consisting of *Pichia stipitis* FPL-UC7 (NRRL Y-21448) and *Pichia stipitis* FPL-PLU20 (NRRL Y-21970).

11. The mutant of claim 9, wherein the mutant is *Pichia stipitis* Shi31 (NRRL Y-30230) or a derivative thereof, the derivative retaining the ability to ferment xylose.

12. A method of producing ethanol from the fermentation of xylose comprising the step of:
culturing a mutant yeast according to claim 4 in xylose-containing material under suitable conditions for a period of time sufficient to allow fermentation of xylose to ethanol.

13. The method of claim 12, wherein reduced expression of SHAM-sensitive terminal oxidase in the mutant yeast is accomplished by means selected from the group consisting of disruption of the SHAM-sensitive terminal oxidase gene and expression of antisense RNA complementary SHAM-sensitive terminal oxidase mRNA.

14. The method of claim 12, wherein the mutant yeast is a *Pichia stipitis* strain.

15. The method of claim 12, wherein the mutant yeast is derived from a *Pichia stipitis* strain selected from the group consisting of FPL-UC7 (NRRL 21448) and FPL-PLU20 (NRRL 21970).

16. The method of claim 12, wherein the mutant yeast is *Pichia stipitis* Shi31 (NRRL Y-30230).

17. A genetic construct comprising a sequence encoding the *Pichia stipits* SHAM-sensitive terminal oxidase of SEQ ID NO:26 operably connected to a promoter expressible in yeast.

18. The genetic construct of claim 17, wherein the polynucleotide sequence comprises SEQ ID NO:25.

19. A recombinant yeast comprising the genetic construct of claim 17, the yeast belonging to a species selected from the group consisting of *Saccharomyces cerevisiae, Saccharomyces carlsbergensis, Saccharomyces byanus, Saccharomyces delbrueckii, Saccharomyces diastaticus, Saccharomyces sake, Saccharomyces thermotolerans, Saccharomyces urvarum*, and Group III species, the Group III species natively comprising an antimycin A-insensitive pathway and a cytochrome pathway.

20. The recombinant yeast of claim 19, wherein the species is *Saccharomyces cerevisiae*.

21. The yeast of claim 19, wherein the species is selected from the group consisting of *Schizosaccharomyces pombe, Candida utilis, Candida parapilosis*, and *Kluyveromyces lactis*.

22. A method of producing ethanol from the fermentation of xylose comprising the step of:
culturing a mutant yeast according to claim 9 in xylose-containing material under suitable conditions for a period of time sufficient to allow fermentation of xylose to ethanol.

23. The method of claim 22, wherein reduced expression of SHAM-sensitive terminal oxidase in the mutant yeast is accomplished by means selected from the group consisting of disruption of the SHAM-sensitive termainal oxidase gene and expression of antisense RNA complementary of SHAM-sensitive terminal oxidase mRNA.

* * * * *

UNITED STATES PATENT AND TRADEMARK OFFICE
CERTIFICATE OF CORRECTION

PATENT NO. : 6,391,599 B1
DATED : May 21, 2002
INVENTOR(S) : Nian-Qing Shi and Thomas W. Jeffries It is certified that error appears in the above-identified patent and that said Letters Patent is hereby corrected as shown below:

Title page,
Item [73], Assignee, "Wisconsin Alumni Research Foundation, Madison, WI (US)" should read -- Wisconsin Alumni Foundation, Madison, WI (US) and The United States of America as Represented by the Secretary of Agriculture, Washington, D.C. (US) --.

Column 37,
Lines 27-35, should read -- 4. An isolated xylose-fermenting mutant of a yeast or fungal species, the mutant having reduced SHAM-sensitive terminal oxidase relative to the level of SHAM-sensitive terminal oxidase in the parent strain from which the mutant was derived, the parent strain comprising SHAM-sensitive terminal oxidase of SEQ ID NO:26. --.
Line 51, "of *Pichia stipitis*," should read -- of a *Pichia stipitis* strain, --.

Signed and Sealed this

Fifteenth Day of March, 2005

JON W. DUDAS
*Director of the United States Patent and Trademark Office*